(12) United States Patent
Schepis et al.

(10) Patent No.: US 12,343,069 B2
(45) Date of Patent: Jul. 1, 2025

(54) EMG GUIDANCE FOR PROBE PLACEMENT, NEARBY TISSUE PRESERVATION, AND LESION CONFIRMATION

(71) Applicant: Avent, Inc., Alpharetta, GA (US)

(72) Inventors: Eric A. Schepis, Alpharetta, GA (US); Sara Kebede, New Orleans, LA (US); Phillip A. Schorr, Cumming, GA (US); David T. Curd, Alpharetta, GA (US); Craig F. Steinman, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 1012 days.

(21) Appl. No.: 16/482,452

(22) PCT Filed: Jan. 25, 2018

(86) PCT No.: PCT/US2018/015127
§ 371 (c)(1),
(2) Date: Jul. 31, 2019

(87) PCT Pub. No.: WO2018/144297
PCT Pub. Date: Aug. 9, 2018

(65) Prior Publication Data
US 2020/0038096 A1  Feb. 6, 2020

Related U.S. Application Data

(60) Provisional application No. 62/453,232, filed on Feb. 1, 2017.

(51) Int. Cl.
*A61B 18/14* (2006.01)
*A61B 5/00* (2006.01)
(Continued)

(52) U.S. Cl.
CPC ............ *A61B 18/148* (2013.01); *A61B 5/296* (2021.01); *A61B 5/6848* (2013.01);
(Continued)

(58) Field of Classification Search
None
See application file for complete search history.

(56) References Cited

U.S. PATENT DOCUMENTS 4,570,640 A   2/1986  Barsa
4,759,377 A   7/1988  Dykstra
(Continued)

FOREIGN PATENT DOCUMENTS

EP          1594401      1/2003
WO    WO 2009/105106 A2  8/2009
(Continued)

OTHER PUBLICATIONS

English Translation of Notice of Refusal issued Oct. 26, 2021, in related JP application No. 2019-541345, 10 pages.
(Continued)

*Primary Examiner* — Sean W Collins
*Assistant Examiner* — Nora W Rhodes
(74) *Attorney, Agent, or Firm* — Meunier Carlin & Curfman LLC

(57) ABSTRACT

A system and method for locating a target nerve associated with a facet joint via nerve stimulation and monitoring of electrical muscle activity in a multifidus muscle adjacent the target nerve are described. The system includes a probe housed within a cannula and comprising a probe electrode; a recording electrode for monitoring electrical muscle activity in a medial fascicle of the multifidus muscle; a signal generator; and a controller coupled to the probe electrode and recording electrode. The controller delivers a nerve stimulation from the signal generator to the nerve via the
(Continued)

probe electrode and monitors electrical muscle activity in the medial fascicle via the recording electrode. The probe's proximity to the nerve is determined by the electrical muscle activity in the medial fascicle elicited as a result of the nerve stimulation, where the controller provides feedback to a user to guide placement of the probe adjacent the nerve.

33 Claims, 17 Drawing Sheets

(51) Int. Cl.
  *A61B 5/296* (2021.01)
  *A61B 18/00* (2006.01)
  *A61N 1/05* (2006.01)

(52) U.S. Cl.
  CPC .. *A61N 1/0551* (2013.01); *A61B 2018/00577* (2013.01); *A61B 2018/00839* (2013.01)

(56) References Cited

U.S. PATENT DOCUMENTS

| | | | |
|---|---|---|---|
| 4,817,628 A | 4/1989 | Zealear et al. | |
| 4,964,411 A | 10/1990 | Johnson et al. | |
| 5,284,153 A | 2/1994 | Raymond et al. | |
| 5,284,154 A | 2/1994 | Raymond et al. | |
| 5,775,331 A | 7/1998 | Raymond et al. | |
| 5,778,145 A | 7/1998 | De Nichilo | |
| 6,181,961 B1 | 1/2001 | Prass | |
| 6,306,100 B1 | 10/2001 | Prass | |
| 6,334,068 B1* | 12/2001 | Hacker | A61B 5/4893 600/545 |
| 6,366,813 B1 | 4/2002 | DiLorenzo | |
| 6,466,817 B1 | 10/2002 | Kaula et al. | |
| 6,500,128 B2 | 12/2002 | Marino | |
| 6,564,078 B1 | 5/2003 | Marino et al. | |
| 6,654,634 B1 | 11/2003 | Prass | |
| 6,760,616 B2 | 7/2004 | Hoey et al. | |
| 6,819,956 B2 | 11/2004 | DiLorenzo | |
| 7,050,848 B2 | 5/2006 | Hoey et al. | |
| 7,079,882 B1 | 7/2006 | Schmidt | |
| 7,079,883 B2 | 7/2006 | Marino et al. | |
| 7,130,673 B2 | 10/2006 | Tolvanen-Laasko et al. | |
| 7,177,677 B2 | 2/2007 | Kaula et al. | |
| 7,207,949 B2 | 4/2007 | Miles et al. | |
| 7,209,787 B2 | 4/2007 | DiLorenzo | |
| 7,214,197 B2 | 5/2007 | Prass | |
| 7,216,001 B2 | 5/2007 | Hacker et al. | |
| 7,231,254 B2 | 6/2007 | DiLorenzo | |
| 7,242,984 B2 | 7/2007 | DiLorenzo | |
| 7,277,758 B2 | 10/2007 | DiLorenzo | |
| 7,283,867 B2 | 10/2007 | Strother et al. | |
| 7,310,546 B2 | 12/2007 | Prass | |
| 7,324,851 B1 | 1/2008 | DiLorenzo | |
| 7,379,767 B2 | 5/2008 | Rea | |
| 7,403,820 B2 | 7/2008 | DiLorenzo | |
| 7,452,335 B2 | 11/2008 | Wells et al. | |
| 7,470,236 B1 | 12/2008 | Kelleher et al. | |
| 7,522,953 B2 | 4/2009 | Kaula et al. | |
| 7,553,307 B2 | 6/2009 | Bleich et al. | |
| 7,555,343 B2 | 6/2009 | Bleich | |
| 7,574,257 B2 | 8/2009 | Rittman, III | |
| 7,582,058 B1 | 9/2009 | Miles et al. | |
| 7,583,991 B2 | 9/2009 | Rea | |
| 7,623,928 B2 | 11/2009 | DiLorenzo | |
| 7,657,308 B2 | 2/2010 | Miles et al. | |
| 7,666,843 B2 | 2/2010 | Benowitz et al. | |
| 7,691,057 B2 | 4/2010 | Miles et al. | |
| 7,693,562 B2 | 4/2010 | Marino et al. | |
| 7,717,932 B2 | 5/2010 | McFarlin et al. | |
| 7,738,968 B2 | 6/2010 | Bleich | |
| 7,738,969 B2 | 6/2010 | Bleich | |
| 7,740,631 B2 | 6/2010 | Bleich et al. | |
| 7,747,325 B2 | 6/2010 | Dilorenzo | |
| 7,811,138 B2 | 10/2010 | Santangelo et al. | |
| 7,819,801 B2 | 10/2010 | Miles et al. | |
| 7,853,326 B2 | 12/2010 | Rittman, III | |
| 7,853,329 B2 | 12/2010 | DiLorenzo | |
| 7,860,570 B2 | 12/2010 | Whitehurst et al. | |
| 7,865,250 B2 | 1/2011 | Mrva et al. | |
| 7,892,173 B2 | 2/2011 | Miles et al. | |
| 7,905,840 B2 | 3/2011 | Pimenta et al. | |
| 7,918,849 B2 | 4/2011 | Bleich et al. | |
| 7,920,922 B2 | 4/2011 | Gharib et al. | |
| 7,930,035 B2 | 4/2011 | DiLorenzo | |
| 7,935,051 B2 | 5/2011 | Miles et al. | |
| 7,959,577 B2 | 6/2011 | Schmitz et al. | |
| 7,962,191 B2 | 6/2011 | Marino et al. | |
| 7,963,915 B2 | 6/2011 | Bleich | |
| 7,963,927 B2 | 6/2011 | Kelleher et al. | |
| 7,974,696 B1 | 7/2011 | DiLorenzo | |
| 7,981,144 B2 | 7/2011 | Geist et al. | |
| 7,987,001 B2 | 7/2011 | Teichman et al. | |
| 7,991,463 B2 | 8/2011 | Kelleher et al. | |
| 7,993,269 B2 | 8/2011 | Donofrio et al. | |
| 8,000,782 B2 | 8/2011 | Gharib et al. | |
| 8,000,785 B2 | 8/2011 | Rittman, III | |
| 8,005,535 B2 | 8/2011 | Gharib et al. | |
| 8,016,767 B2 | 9/2011 | Miles et al. | |
| 8,016,846 B2 | 9/2011 | McFarlin et al. | |
| 8,027,716 B2 | 9/2011 | Gharib et al. | |
| 8,050,769 B2 | 11/2011 | Gharib et al. | |
| 8,052,688 B2 | 11/2011 | Wolf, II | |
| 8,055,349 B2 | 11/2011 | Gharib et al. | |
| 8,062,298 B2 | 11/2011 | Schmitz et al. | |
| 8,062,300 B2 | 11/2011 | Schmitz et al. | |
| 8,068,912 B2 | 11/2011 | Kaula et al. | |
| 8,083,685 B2 | 12/2011 | Fagin et al. | |
| 8,090,436 B2 | 1/2012 | Hoey et al. | |
| 8,114,019 B2 | 2/2012 | Miles et al. | |
| 8,133,173 B2 | 3/2012 | Miles et al. | |
| 8,137,284 B2 | 3/2012 | Miles et al. | |
| 8,147,421 B2 | 4/2012 | Farquhar et al. | |
| 8,160,695 B2 | 4/2012 | Dacey, Jr. et al. | |
| 8,165,653 B2 | 4/2012 | Marino et al. | |
| 8,165,668 B2 | 4/2012 | Dacey, Jr. et al. | |
| 8,165,669 B2 | 4/2012 | Dacey, Jr. et al. | |
| 8,170,658 B2 | 5/2012 | Dacey, Jr. et al. | |
| 8,170,659 B2 | 5/2012 | Dacey, Jr. et al. | |
| 8,170,660 B2 | 5/2012 | Dacey, Jr. et al. | |
| 8,172,750 B2 | 5/2012 | Miles et al. | |
| 8,180,446 B2 | 5/2012 | Dacey, Jr. et al. | |
| 8,180,447 B2 | 5/2012 | Dacey, Jr. et al. | |
| 8,182,423 B2 | 5/2012 | Miles et al. | |
| 8,187,179 B2 | 5/2012 | Miles et al. | |
| 8,192,326 B2 | 6/2012 | Miles et al. | |
| 8,192,357 B2 | 6/2012 | Miles et al. | |
| 8,192,435 B2 | 6/2012 | Bleich et al. | |
| 8,195,287 B2 | 6/2012 | Dacey, Jr. et al. | |
| 8,195,304 B2 | 6/2012 | Strother et al. | |
| 8,206,312 B2 | 6/2012 | Farquhar | |
| 8,221,397 B2 | 7/2012 | Bleich et al. | |
| 8,233,976 B2 | 7/2012 | Dacey, Jr. et al. | |
| 8,241,313 B2 | 8/2012 | McFarlin et al. | |
| 8,244,343 B2 | 8/2012 | Gharib et al. | |
| 8,255,044 B2 | 8/2012 | Miles et al. | |
| 8,255,045 B2 | 8/2012 | Gharib et al. | |
| 8,262,683 B2 | 9/2012 | McFarlin et al. | |
| 8,265,744 B2 | 9/2012 | Gharib et al. | |
| 8,265,747 B2 | 9/2012 | Rittman, III et al. | |
| 8,298,216 B2 | 10/2012 | Burger et al. | |
| 8,303,498 B2 | 11/2012 | Miles et al. | |
| 8,303,515 B2 | 11/2012 | Miles et al. | |
| 8,303,516 B2 | 11/2012 | Schmitz et al. | |
| 8,313,430 B1 | 11/2012 | Pimenta | |
| 8,323,208 B2 | 12/2012 | Davis et al. | |
| 8,326,414 B2 | 12/2012 | Neubardt et al. | |
| 8,337,410 B2 | 12/2012 | Kelleber et al. | |
| 8,343,046 B2 | 1/2013 | Miles et al. | |
| 8,343,065 B2 | 1/2013 | Bartol et al. | |
| 8,343,079 B2 | 1/2013 | Bartol et al. | |
| 8,355,780 B2 | 1/2013 | Miles et al. | |
| 8,374,673 B2 | 2/2013 | Adcox et al. | |

(56) References Cited

U.S. PATENT DOCUMENTS

| | | |
|---|---|---|
| 8,388,527 B2 | 3/2013 | Miles et al. |
| 8,396,557 B2 | 3/2013 | DiLorenzo |
| 8,401,632 B1 | 3/2013 | Stone et al. |
| 8,403,841 B2 | 3/2013 | Miles et al. |
| 8,412,338 B2 | 4/2013 | Faltys |
| 8,439,832 B2 | 5/2013 | Miles et al. |
| 8,439,845 B2 | 5/2013 | Folkerts et al. |
| 8,442,621 B2 | 5/2013 | Gorek et al. |
| 8,444,571 B2 | 5/2013 | Folkerts et al. |
| 8,452,370 B2 | 5/2013 | Prass |
| 8,465,513 B2 | 6/2013 | McFarlin et al. |
| 8,489,170 B2 | 7/2013 | Marino et al. |
| 8,500,634 B2 | 8/2013 | Miles et al. |
| 8,500,653 B2 | 8/2013 | Farquhar |
| 8,500,738 B2 | 8/2013 | Wolf, II |
| 8,512,235 B2 | 8/2013 | Miles et al. |
| 8,512,715 B2 | 8/2013 | Papay |
| 8,515,520 B2 | 8/2013 | Brunnett et al. |
| 8,517,954 B2 | 8/2013 | Bartol et al. |
| 8,523,768 B2 | 9/2013 | Miles et al. |
| 8,538,539 B2 | 9/2013 | Gharib et al. |
| 8,548,579 B2 | 10/2013 | Gharib et al. |
| 8,548,604 B2 | 10/2013 | Whitehurst et al. |
| 8,550,994 B2 | 10/2013 | Miles et al. |
| 8,556,808 B2 | 10/2013 | Miles et al. |
| 8,560,062 B2 | 10/2013 | Rittman, III et al. |
| 8,562,521 B2 | 10/2013 | Miles et al. |
| 8,562,539 B2 | 10/2013 | Marino |
| 8,568,317 B1 | 10/2013 | Gharib et al. |
| 8,568,416 B2 | 10/2013 | Schmitz et al. |
| 8,579,902 B2 | 11/2013 | Bleich et al. |
| 8,585,704 B2 | 11/2013 | Schmitz et al. |
| 8,591,431 B2 | 11/2013 | Calancie et al. |
| 8,591,432 B2 | 11/2013 | Pimenta et al. |
| 8,594,805 B2 | 11/2013 | Hincapie Ordonez et al. |
| 8,602,982 B2 | 12/2013 | Miles et al. |
| 8,612,002 B2 | 12/2013 | Faltys et al. |
| 8,613,745 B2 | 12/2013 | Bleich |
| 8,617,163 B2 | 12/2013 | Bleich |
| 8,617,228 B2 | 12/2013 | Wittenberger et al. |
| 8,628,469 B2 | 1/2014 | Miles et al. |
| 8,630,706 B2 | 1/2014 | Dacey, Jr. et al. |
| 8,634,904 B2 | 1/2014 | Kaula et al. |
| 8,641,638 B2 | 2/2014 | Kelleher et al. |
| 8,647,346 B2 | 2/2014 | Bleich et al. |
| 8,649,866 B2 | 2/2014 | Brooke |
| 8,663,100 B2 | 3/2014 | Miles et al. |
| 8,672,840 B2 | 3/2014 | Miles et al. |
| 8,679,006 B2 | 3/2014 | Miles et al. |
| 8,680,986 B2 | 3/2014 | Costantino |
| 8,688,237 B2 | 4/2014 | Stanislaus et al. |
| 8,696,559 B2 | 4/2014 | Miles et al. |
| 8,706,235 B2 | 4/2014 | Karamanoglu et al. |
| 8,708,899 B2 | 4/2014 | Miles et al. |
| 8,715,275 B2 | 5/2014 | Burger et al. |
| 8,738,123 B2 | 5/2014 | Gharib et al. |
| 8,740,783 B2 | 6/2014 | Gharib et al. |
| 8,747,307 B2 | 6/2014 | Miles et al. |
| 8,753,270 B2 | 6/2014 | Miles et al. |
| 8,753,271 B1 | 6/2014 | Miles et al. |
| 8,755,893 B2 | 6/2014 | Gross et al. |
| 8,758,378 B2 | 6/2014 | McFarlin et al. |
| 8,762,065 B2 | 6/2014 | DiLorenzo |
| 8,764,649 B2 | 7/2014 | Miles et al. |
| 8,768,450 B2 | 7/2014 | Gharib et al. |
| 8,781,597 B2 | 7/2014 | DiLorenzo |
| 8,788,045 B2 | 7/2014 | Gross et al. |
| 8,801,626 B2 | 8/2014 | Sun et al. |
| 8,805,518 B2 | 8/2014 | King et al. |
| 8,805,533 B2 | 8/2014 | Boggs, II et al. |
| 8,812,116 B2 | 8/2014 | Kaula et al. |
| 8,818,503 B2 | 8/2014 | Rittman, III |
| 8,818,524 B2 | 8/2014 | Hincapie Ordonez et al. |
| 8,821,396 B1 | 9/2014 | Miles et al. |
| 8,827,900 B1 | 9/2014 | Pimenta |
| 8,845,545 B2 | 9/2014 | Folkerts et al. |
| 8,855,767 B2 | 10/2014 | Faltys et al. |
| 8,876,904 B2 | 11/2014 | Pimenta et al. |
| 8,882,679 B2 | 11/2014 | Bartol et al. |
| 8,886,280 B2 | 11/2014 | Kartush |
| 8,886,339 B2 | 11/2014 | Faltys et al. |
| 8,897,882 B2 | 11/2014 | Nakatomi et al. |
| 8,915,846 B2 | 12/2014 | Miles et al. |
| 8,920,816 B2 | 12/2014 | Papay |
| 8,932,312 B2 | 1/2015 | McFarlin et al. |
| 8,942,797 B2 | 1/2015 | Bartol et al. |
| 8,942,801 B2 | 1/2015 | Miles et al. |
| 8,945,004 B2 | 2/2015 | Miles et al. |
| 8,945,164 B2 | 2/2015 | Brunnett et al. |
| 8,956,283 B2 | 2/2015 | Miles et al. |
| 8,958,869 B2 | 2/2015 | Kelleher et al. |
| 8,977,352 B2 | 3/2015 | Gharib et al. |
| 8,979,767 B2 | 3/2015 | Bartol et al. |
| 8,983,593 B2 | 3/2015 | Bartol et al. |
| 8,989,855 B2 | 3/2015 | Murphy et al. |
| 8,989,858 B2 | 3/2015 | Dacey, Jr. et al. |
| 8,989,866 B2 | 3/2015 | Gharib et al. |
| 8,996,112 B2 | 3/2015 | Brooke |
| 8,996,169 B2 | 3/2015 | Lightcap et al. |
| 9,008,793 B1 | 4/2015 | Cosman, Sr. et al. |
| 9,014,776 B2 | 4/2015 | Marino et al. |
| 9,014,802 B2 | 4/2015 | Dacey, Jr. et al. |
| 9,020,591 B2 | 4/2015 | Dacey, Jr. et al. |
| 9,020,592 B2 | 4/2015 | Dacey, Jr. et al. |
| 9,031,658 B2 | 5/2015 | Chiao et al. |
| 9,037,226 B2 | 5/2015 | Hacker et al. |
| 9,037,250 B2 | 5/2015 | Kaula et al. |
| 9,042,988 B2 | 5/2015 | DiLorenzo |
| 9,050,005 B2 | 6/2015 | Ignagni et al. |
| 9,066,701 B1 | 6/2015 | Finley et al. |
| 9,084,550 B1 | 7/2015 | Bartol et al. |
| 9,084,551 B2 | 7/2015 | Brunnett et al. |
| 9,101,346 B2 | 8/2015 | Burger et al. |
| 9,113,801 B2 | 8/2015 | DiLorenzo |
| 9,113,912 B1 | 8/2015 | Mehta et al. |
| 9,119,572 B2 | 9/2015 | Gorek et al. |
| 9,131,947 B2 | 9/2015 | Ferree |
| 9,132,217 B2 | 9/2015 | Soykan et al. |
| 9,138,217 B2 | 9/2015 | Smith et al. |
| 9,155,503 B2 | 10/2015 | Cadwell |
| 9,162,064 B2 | 10/2015 | Faltys et al. |
| 9,174,041 B2 | 11/2015 | Faltys et al. |
| 9,204,871 B2 | 12/2015 | Miles et al. |
| 9,204,925 B2 | 12/2015 | Papay |
| 9,232,906 B2 | 1/2016 | Wolf, II |
| 9,247,952 B2 | 2/2016 | Bleich et al. |
| 9,248,278 B2 | 2/2016 | Crosby et al. |
| 9,259,144 B2 | 2/2016 | Smith et al. |
| 9,265,490 B2 | 2/2016 | Bowman et al. |
| 9,265,493 B2 | 2/2016 | Miles et al. |
| 9,265,562 B2 | 2/2016 | Papay |
| 9,265,932 B2 | 2/2016 | Martens et al. |
| 9,272,151 B2 | 3/2016 | Sijko et al. |
| 9,283,394 B2 | 3/2016 | Whitehurst et al. |
| 9,295,396 B2 | 3/2016 | Gharib et al. |
| 9,295,401 B2 | 3/2016 | Cadwell |
| 9,301,711 B2 | 4/2016 | Bartol et al. |
| 9,301,743 B2 | 4/2016 | Miles et al. |
| 9,314,152 B2 | 4/2016 | Pimenta et al. |
| 9,314,627 B2 | 4/2016 | Arcot-Krishnamurthy et al. |
| 9,320,618 B2 | 4/2016 | Schmitz et al. |
| 9,320,900 B2 | 4/2016 | DiLorenzo |
| 9,333,363 B2 | 5/2016 | Hoffer et al. |
| 9,339,263 B2 | 5/2016 | Fenn et al. |
| 9,345,880 B1 | 5/2016 | DiLorenzo |
| 9,351,741 B2 | 5/2016 | Schmitz et al. |
| 9,352,146 B2 | 5/2016 | Langhals et al. |
| 9,352,160 B2 | 5/2016 | Brooke |
| 9,357,573 B2 | 6/2016 | Dilorenzo |
| 9,358,374 B2 | 6/2016 | Dacey, Jr. et al. |
| 9,364,164 B2 | 6/2016 | Lacoste |
| 9,392,953 B1 | 7/2016 | Gharib |
| 9,392,955 B2 | 7/2016 | Folkerts et al. |
| 9,398,931 B2 | 7/2016 | Wittenberger et al. |

(56) References Cited

U.S. PATENT DOCUMENTS

| | | |
|---|---|---|
| 9,402,558 B2 | 8/2016 | John et al. |
| 9,743,853 B2 | 8/2017 | Kelleher et al. |
| 2003/0105503 A1 | 6/2003 | Marino |
| 2004/0015204 A1 | 1/2004 | Whitehurst et al. |
| 2004/0015205 A1 | 1/2004 | Whitehurst et al. |
| 2004/0122482 A1 | 6/2004 | Tung et al. |
| 2004/0225228 A1 | 11/2004 | Ferree |
| 2004/0254494 A1 | 12/2004 | Spokoyny |
| 2004/0260357 A1 | 12/2004 | Vaughan et al. |
| 2004/0260358 A1 | 12/2004 | Vaughan et al. |
| 2005/0004623 A1 | 1/2005 | Patrick et al. |
| 2005/0192645 A1 | 9/2005 | Stein et al. |
| 2005/0283148 A1* | 12/2005 | Janssen .............. A61B 18/16 606/50 |
| 2006/0089609 A1 | 4/2006 | Bleich et al. |
| 2006/0089633 A1 | 4/2006 | L. Bleich et al. |
| 2006/0089640 A1 | 4/2006 | Bleich et al. |
| 2006/0095028 A1 | 5/2006 | Bleich |
| 2006/0122458 A1 | 6/2006 | Bleich |
| 2006/0149345 A1 | 7/2006 | Boggs, II et al. |
| 2006/0224078 A1 | 10/2006 | Hoey et al. |
| 2006/0224223 A1* | 10/2006 | Podhajsky ............ A61B 18/148 607/117 |
| 2006/0276702 A1 | 12/2006 | McGinnis |
| 2006/0276704 A1 | 12/2006 | McGinnis et al. |
| 2006/0276720 A1 | 12/2006 | McGinnis et al. |
| 2006/0276721 A1 | 12/2006 | McGinnis |
| 2007/0015985 A1 | 1/2007 | Tolvanen-Laasko et al. |
| 2007/0043405 A1 | 2/2007 | Rittman, III |
| 2007/0118044 A1 | 5/2007 | Remes et al. |
| 2007/0213734 A1 | 9/2007 | Bleich et al. |
| 2007/0281988 A1 | 12/2007 | Cameron et al. |
| 2007/0282217 A1 | 12/2007 | McGinnis et al. |
| 2008/0065178 A1 | 3/2008 | Kelleher et al. |
| 2008/0066770 A1 | 3/2008 | Olmos |
| 2008/0071191 A1 | 3/2008 | Kelleher et al. |
| 2008/0133016 A1 | 6/2008 | Heinz |
| 2008/0147084 A1 | 6/2008 | Bleich et al. |
| 2008/0183074 A1 | 7/2008 | Carls et al. |
| 2008/0287820 A1 | 11/2008 | Ignagni et al. |
| 2008/0312660 A1 | 12/2008 | Bleich et al. |
| 2009/0018399 A1 | 1/2009 | Martinelli et al. |
| 2009/0018507 A1 | 1/2009 | Schmitz et al. |
| 2009/0024124 A1* | 1/2009 | Lefler ................ A61B 18/1482 606/41 |
| 2009/0036799 A1 | 2/2009 | Sandhu et al. |
| 2009/0048531 A1 | 2/2009 | McGinnis et al. |
| 2009/0105788 A1 | 4/2009 | Bartol et al. |
| 2009/0118780 A1 | 5/2009 | DiLorenzo |
| 2009/0149797 A1 | 6/2009 | Dacey, Jr. et al. |
| 2009/0149799 A1 | 6/2009 | Dacey, Jr. et al. |
| 2009/0171381 A1 | 7/2009 | Schmitz et al. |
| 2009/0177112 A1 | 7/2009 | Gharib et al. |
| 2009/0187230 A1 | 7/2009 | Dilorenzo |
| 2009/0275997 A1 | 11/2009 | Faltys et al. |
| 2010/0001864 A1 | 1/2010 | O'Brien et al. |
| 2010/0004949 A1 | 1/2010 | O'Brien |
| 2010/0010367 A1 | 1/2010 | Foley et al. |
| 2010/0023089 A1 | 1/2010 | DiLorenzo |
| 2010/0052276 A1 | 3/2010 | Kartush |
| 2010/0094231 A1 | 4/2010 | Bleich et al. |
| 2010/0106145 A1 | 4/2010 | Widgerow |
| 2010/0145178 A1 | 6/2010 | Kartush |
| 2010/0152812 A1 | 6/2010 | Flaherty et al. |
| 2010/0249639 A1 | 9/2010 | Bhatt |
| 2010/0317989 A1 | 12/2010 | Gharib et al. |
| 2010/0331883 A1 | 12/2010 | Schmitz et al. |
| 2011/0004207 A1 | 1/2011 | Wallace et al. |
| 2011/0028860 A1 | 2/2011 | Chenaux et al. |
| 2011/0166519 A1* | 7/2011 | Nguyen ................ A61N 1/403 604/114 |
| 2011/0301593 A1 | 12/2011 | Teichman et al. |
| 2011/0313312 A1 | 12/2011 | Hoey et al. |
| 2012/0029382 A1 | 2/2012 | Kelleher et al. |
| 2012/0059275 A1 | 3/2012 | Fagin et al. |
| 2012/0089153 A1 | 4/2012 | Christopherson et al. |
| 2012/0095360 A1 | 4/2012 | Runney et al. |
| 2012/0123292 A1 | 5/2012 | Fagin et al. |
| 2012/0130269 A1 | 5/2012 | Rea |
| 2012/0136413 A1 | 5/2012 | Bonde et al. |
| 2012/0143206 A1 | 6/2012 | Wallace et al. |
| 2012/0150063 A1 | 6/2012 | Rea |
| 2012/0191003 A1 | 7/2012 | Garabedian et al. |
| 2012/0259239 A1 | 10/2012 | Chenaux et al. |
| 2012/0277548 A1 | 11/2012 | Burton |
| 2012/0296230 A1 | 11/2012 | Davis et al. |
| 2013/0012831 A1 | 1/2013 | Schmitz et al. |
| 2013/0053853 A1 | 2/2013 | Schmitz et al. |
| 2013/0150970 A1 | 6/2013 | Thaiyananthan |
| 2013/0204097 A1 | 8/2013 | Rondoni et al. |
| 2013/0245722 A1 | 9/2013 | Ternes et al. |
| 2013/0253296 A1 | 9/2013 | Prass |
| 2013/0253599 A1 | 9/2013 | Gorek et al. |
| 2013/0310830 A1 | 11/2013 | Wolf, II |
| 2013/0338466 A1 | 12/2013 | Stone et al. |
| 2013/0338749 A1 | 12/2013 | Brunnett et al. |
| 2013/0345718 A1 | 12/2013 | Crawford et al. |
| 2014/0005763 A1 | 1/2014 | Cederna et al. |
| 2014/0018695 A1 | 1/2014 | Farquhar |
| 2014/0039264 A1 | 2/2014 | Heiman |
| 2014/0081358 A1 | 3/2014 | Kelm et al. |
| 2014/0088442 A1 | 3/2014 | Soykan et al. |
| 2014/0114168 A1 | 4/2014 | Block et al. |
| 2014/0135584 A1 | 5/2014 | Lee et al. |
| 2014/0148650 A1 | 5/2014 | Miles et al. |
| 2014/0155720 A1 | 6/2014 | Stanislaus et al. |
| 2014/0163411 A1 | 6/2014 | Rea |
| 2014/0180293 A1 | 6/2014 | Schmitz et al. |
| 2014/0235950 A1 | 8/2014 | Miles et al. |
| 2014/0236144 A1* | 8/2014 | Krueger ............ A61B 18/1477 606/41 |
| 2014/0243823 A1* | 8/2014 | Godara ............ A61B 18/1477 606/49 |
| 2014/0275926 A1* | 9/2014 | Scott ...................... A61B 5/388 600/377 |
| 2014/0288374 A1 | 9/2014 | Miles et al. |
| 2014/0288375 A1 | 9/2014 | Miles et al. |
| 2014/0288389 A1 | 9/2014 | Gharib et al. |
| 2014/0303666 A1 | 10/2014 | Heiman et al. |
| 2014/0316268 A1* | 10/2014 | Kafiluddi ............ A61B 5/296 606/34 |
| 2014/0324129 A1 | 10/2014 | Franke et al. |
| 2014/0350636 A1 | 11/2014 | King et al. |
| 2014/0378999 A1 | 12/2014 | Crawford et al. |
| 2015/0011843 A1 | 1/2015 | Toth et al. |
| 2015/0032022 A1 | 1/2015 | Stone et al. |
| 2015/0057564 A1 | 2/2015 | Kim |
| 2015/0057711 A1 | 2/2015 | Kim |
| 2015/0088030 A1 | 3/2015 | Taylor |
| 2015/0112325 A1 | 4/2015 | Whitman |
| 2015/0119874 A1 | 4/2015 | Brunnett et al. |
| 2015/0119989 A1 | 4/2015 | Pimenta et al. |
| 2015/0133734 A1 | 5/2015 | Miles et al. |
| 2015/0133911 A1* | 5/2015 | Batchelor ............ A61B 18/1206 606/34 |
| 2015/0150693 A1 | 6/2015 | Gharib et al. |
| 2015/0157227 A1 | 6/2015 | Kelleher et al. |
| 2015/0157228 A1* | 6/2015 | Marino ............ A61B 17/3423 600/202 |
| 2015/0157237 A1 | 6/2015 | Murphy et al. |
| 2015/0164401 A1 | 6/2015 | Toth et al. |
| 2015/0173673 A1 | 6/2015 | Toth et al. |
| 2015/0216478 A1 | 8/2015 | Kaula et al. |
| 2015/0223720 A1 | 8/2015 | Leschinsky et al. |
| 2015/0224326 A1 | 8/2015 | Toth et al. |
| 2015/0230749 A1 | 8/2015 | Gharib et al. |
| 2015/0241447 A1 | 8/2015 | Zitnik et al. |
| 2015/0250423 A1 | 9/2015 | Hacker et al. |
| 2015/0289929 A1 | 10/2015 | Toth et al. |
| 2015/0297139 A1 | 10/2015 | Toth |
| 2015/0313512 A1 | 11/2015 | Hausman et al. |
| 2015/0320329 A1 | 11/2015 | Brunnett et al. |
| 2015/0321000 A1 | 11/2015 | Rosenbluth et al. |
| 2015/0034262 A1 | 12/2015 | Jackson, III |

(56) References Cited

U.S. PATENT DOCUMENTS

| | | |
|---|---|---|
| 2015/0342521 A1 | 12/2015 | Narita et al. |
| 2015/0366630 A1 | 12/2015 | Gorek et al. |
| 2015/0374992 A1 | 12/2015 | Crosby et al. |
| 2016/0000601 A1 | 1/2016 | Burger et al. |
| 2016/0029960 A1 | 2/2016 | Toth et al. |
| 2016/0038072 A1 | 2/2016 | Brown et al. |
| 2016/0038073 A1 | 2/2016 | Brown et al. |
| 2016/0038074 A1 | 2/2016 | Brown et al. |
| 2016/0038745 A1 | 2/2016 | Faltys et al. |
| 2016/0045724 A1 | 2/2016 | Lee et al. |
| 2016/0045746 A1 | 2/2016 | Jiang et al. |
| 2016/0045747 A1 | 2/2016 | Jiang et al. |
| 2016/0045751 A1 | 2/2016 | Jiang et al. |
| 2016/0051319 A1 | 2/2016 | Papay |
| 2016/0051812 A1 | 2/2016 | Montgomery, Jr. et al. |
| 2016/0051813 A1 | 2/2016 | Faltys et al. |
| 2016/0058613 A1 | 3/2016 | Palazzolo et al. |
| 2016/0067497 A1 | 3/2016 | Levine et al. |
| 2016/0081570 A1 | 3/2016 | Farquhar |
| 2016/0081621 A1 | 3/2016 | Cadwell |
| 2016/0081682 A1 | 3/2016 | Miles et al. |
| 2016/0082179 A1 | 3/2016 | Toth et al. |
| 2016/0082180 A1 | 3/2016 | Toth et al. |
| 2016/0114165 A1 | 4/2016 | Levine et al. |
| 2016/0114167 A1 | 4/2016 | Jiang et al. |
| 2016/0120530 A1 | 5/2016 | Miles et al. |
| 2016/0121104 A1 | 5/2016 | Bartol |
| 2016/0121105 A1 | 5/2016 | Lee et al. |
| 2016/0121123 A1 | 5/2016 | Jiang et al. |
| 2016/0128599 A1 | 5/2016 | Rea |
| 2016/0135834 A1 | 5/2016 | Bleich et al. |
| 2016/0143556 A1 | 5/2016 | Farquhar et al. |
| 2016/0150993 A1 | 6/2016 | Powell et al. |
| 2016/0151626 A1 | 6/2016 | Gorman et al. |
| 2016/0166799 A1 | 6/2016 | Papay |
| 2016/0174861 A1 | 6/2016 | Cadwell |
| 2016/0174958 A1 | 6/2016 | Miles et al. |
| 2016/0174959 A1 | 6/2016 | Miles et al. |
| 2016/0192921 A1 | 7/2016 | Pimenta et al. |
| 2016/0199112 A1 | 7/2016 | Kim |
| 2016/0199653 A1 | 7/2016 | Arcot-Krishnamurthy et al. |
| 2016/0199657 A1 | 7/2016 | Jiang et al. |
| 2016/0199658 A1 | 7/2016 | Nassif et al. |
| 2016/0199659 A1 | 7/2016 | Jiang et al. |
| 2016/0206363 A1* | 7/2016 | Mehta .................. A61M 19/00 |
| 2016/0206890 A1 | 7/2016 | Oron et al. |
| 2016/0213313 A1 | 7/2016 | Toth et al. |
| 2018/0021577 A1* | 1/2018 | Phillips ................ A61N 1/0472 |
| | | 604/507 |

FOREIGN PATENT DOCUMENTS

| | | |
|---|---|---|
| WO | WO 2009/130515 A2 | 10/2009 |
| WO | WO 2012/168453 A1 | 12/2012 |
| WO | WO 2015/153487 A1 | 10/2015 |
| WO | WO 2016/014444 A1 | 1/2016 |
| WO | WO 2016/014750 A1 | 1/2016 |
| WO | WO 2016/032929 A2 | 3/2016 |
| WO | WO 2016/032931 A1 | 3/2016 |
| WO | WO 2016/081566 A1 | 5/2016 |

OTHER PUBLICATIONS

International Search Report and Written Opinion for PCT/US2018/015127, dated May 14, 2018, 16 pages.

* cited by examiner

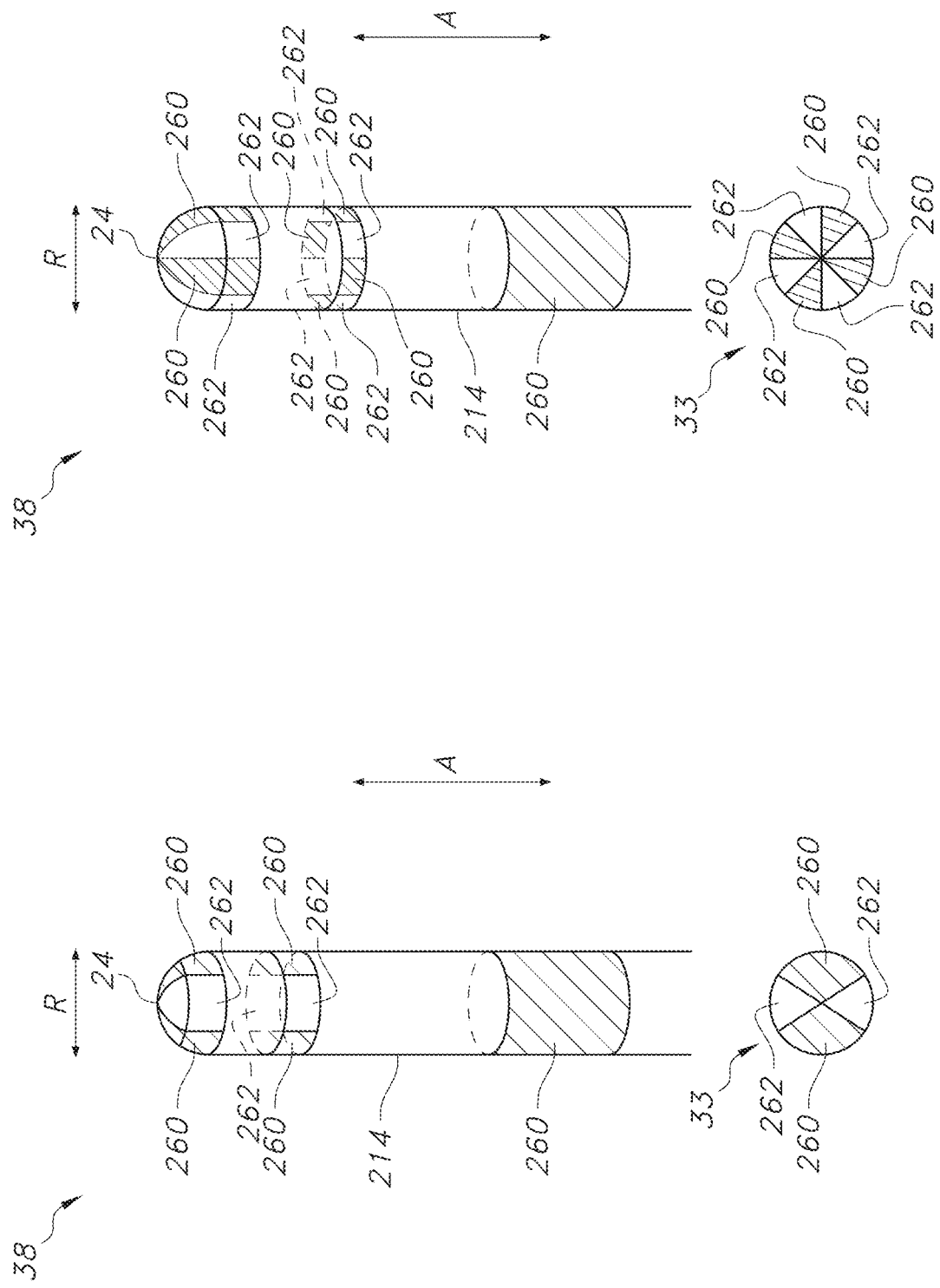

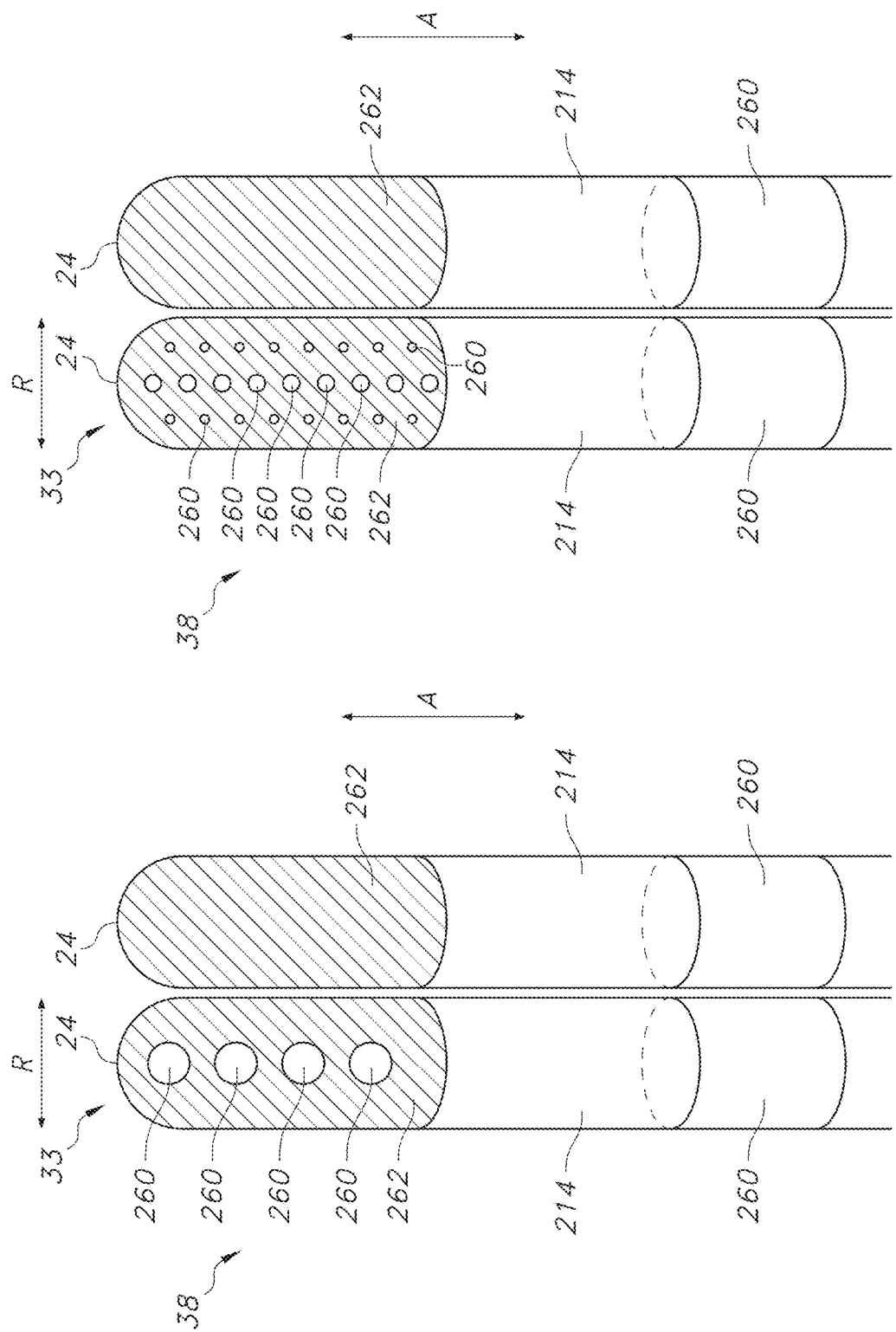

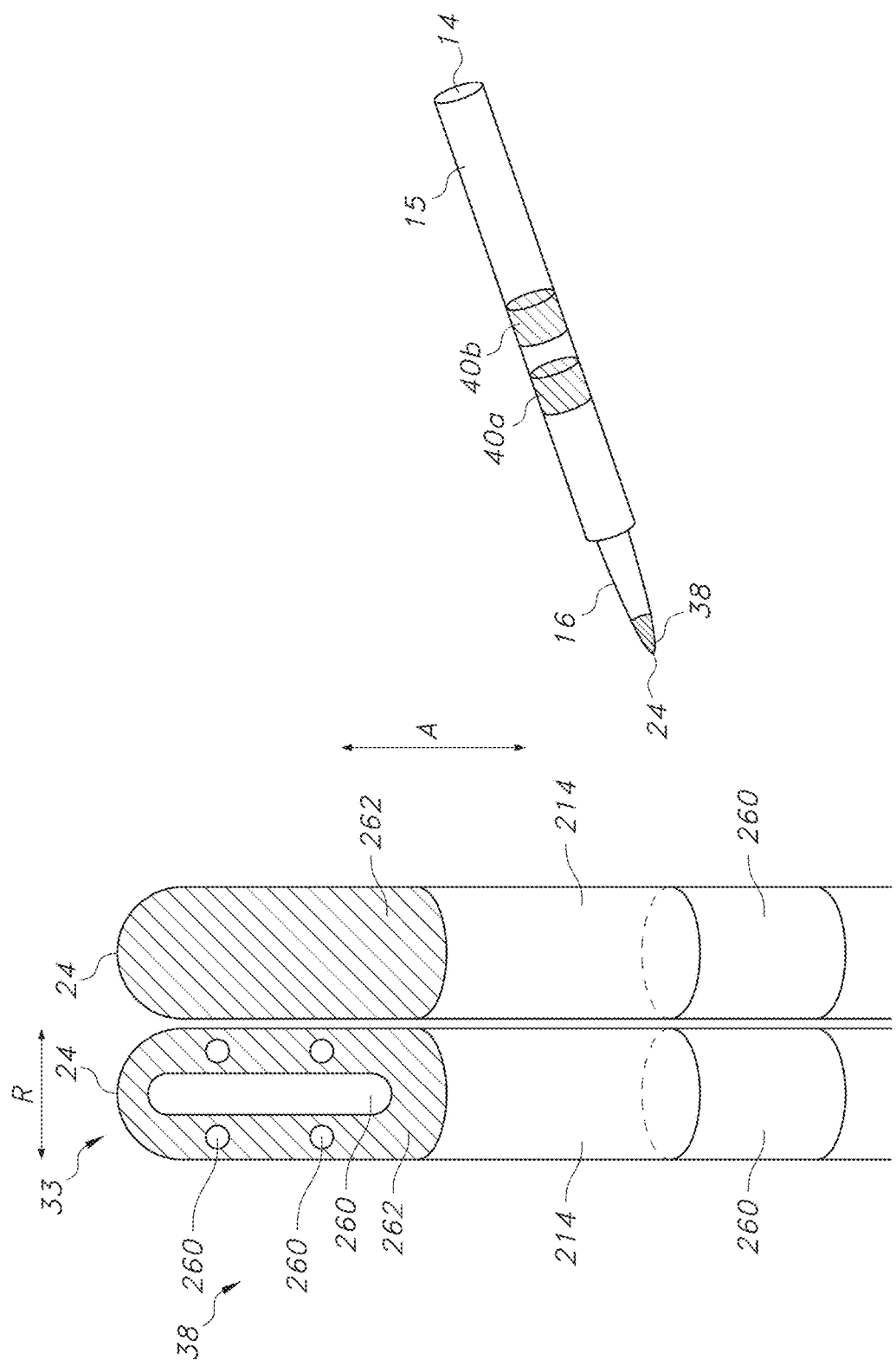

EMG GUIDANCE FOR PROBE PLACEMENT, NEARBY TISSUE PRESERVATION, AND LESION CONFIRMATION

RELATED APPLICATION

The present application is the national stage entry of International Patent Application No. PCT/US2018/015127, having a filing date of Jan. 25, 2018, which claims priority to U.S. Provisional Application Ser. No. 62/453,232, filed on Feb. 1, 2017, both of which are incorporated herein in their entirety by reference thereto.

BACKGROUND OF THE INVENTION

Radiofrequency (RF) ablation is a medical procedure used to destroy biological tissue, including tumor tissue, abnormal cardiac pathways, and nerves that carry intractable pain. RF ablation treats pain by destroying a segment of a nerve that is interposed between the pain source and the brain. That is, RF ablation is used to generate a lesion in nervous tissue that interrupts the transmission of painful signals from passing to higher-order centers required for pain perception.

A typical ablation system includes a needle-like introducer, ablation probe, RF generator, support cables, and a grounding pad that is fastened to the patient's skin. The introducer consists of a stylet that is installed within an electrically insulated cannula. The introducer's stylet is removed during the procedure and replaced by the ablative probe. The probe has an un-insulated region that is located at the probe's tip (i.e., active tip) and is purposed to deliver electrical current to tissue that is produced by the RF generator. The dimensions (e.g., gauges, lengths, active tip lengths) of the introducer and ablative probe are contoured to match the anatomy of the intended ablative site. For example, ablative probes that are used for cervical nerve ablation generally have a smaller active tip (e.g., about a 5 millimeter (mm) diameter) than probes that are used to treat nerves originating from the lumbar spine, which have about a 10 mm diameter active tip.

RF ablation procedures are mostly performed in an outpatient setting, and begin by passing the introducer through the skin and positioning its tip near the site that is targeted for ablation. The introducer is mostly placed under fluoroscopic guidance, and less often, with ultrasonography or with a combination of both modalities. After initial placement, the introducer's stylet is removed and replaced by the ablative probe. The probe's position is verified and fine-tuned by electrically stimulating through the probe's active tip. Electrical stimulation is used to verify that the probe is indeed nearby the target tissue and safely removed from non-target tissue (i.e., spinal nerve root). Sensory electrical stimulation delivered at about 50 hertz (Hz) will elicit a buzzing sensation in the structures that are innervated by the stimulated nerve and may include those nerves in the targeted pain regions. Sensations elicited at stimulation intensities less than 0.5 volts (V) suggest that the activated sensory nerves are in electrical proximity to the probe and can be ablated. Motor electrical stimulation delivered at about 2 Hz through an ideally placed probe will elicit paraspinal muscle contractions identified on visual inspection of the patient's lower back. If the probe is grossly misplaced, however, and is too close to a spinal nerve root, then sensory stimulation will elicit a shooting or radiating sensation down the leg and motor stimulation will elicit a lower limb muscle contraction, where ablation of a lumbar spinal nerve root would cause sensory and motor deficits in the leg. After the probe's location is verified, local anesthetics are deposited to the ablative site (e.g., about 1 milliliter (mL) of 0.5% bupivacaine per ablation site) to reduce the discomfort caused by the lesion, the ablation is performed, and the probes are removed from the patient. The physician does not have immediate verification that the lesion has destroyed the target nerve.

Typically, a lesion is formed around the probe's active tip by heating the tissue surround the tip to temperatures above 45° C., causing protein coagulation and cellular death. Radiofrequency ablation heats tissue by driving an electrical current between the probe's active tip and a cutaneously placed grounding pad for monopolar ablation, or between the probe's active tip and the active tip of a second probe for bipolar ablation, placed nearby. The electrical current vibrates ions located in the surrounding tissue causing molecular friction, and, subsequently, heat. A thermocouple is attached to the probe and positioned within the thermal field. The thermocouple measures the temperatures within the thermal field and uses the temperature measurements to control the amount of electrical power that is delivered to the tissue. That is, the user sets the ablation temperature and the generator modulates the electrical power that is delivered to the tissue necessary to maintain the chosen temperature. Alternatively, RF ablation can be performed without temperature feedback in a feedforward paradigm, where the user sets the ablative power. Lesions are not formed around the grounding pad since its surface area is very large (i.e., low current density) and is located a distance away from the active tip, nor are they formed around the electrically insulated portions of the probe or cannula.

Despite the various contours and geometries that have been developed for the RF ablation probes used to carry out the procedure described above, as well as the imaging and electrical stimulation routines that are used to verify the probe is accurately positioned at or adjacent the target nerve, placement of the RF ablation probe is still a challenge, and inaccurate placement can result in sub-optimal treatment, including the ablation of non-target nerves. Furthermore, the imaging and electrical stimulation modalities that are used today do not confirm that the target nerve hosts the painful signals requiring therapy and cannot be used intraoperatively to confirm treatment success.

Fluoroscopy and ultrasonography are the two most prominent methods used to place the introducer and probe. Fluoroscopy however, cannot image nervous tissue, leaving the physician with bony landmarks to guide the introducer and probe to the target site. However, the technique of ultrasonography can indeed image nerves. Despite this, it is poorly suited to image the nerves that are targeted by RF ablation procedures, since such target nerves are small, deep, and located near bone.

Further, known electrical stimulation methodologies are effective at showing a grossly positioned probe as described above, but these methodologies cannot confirm that the probe is sufficiently placed to ablate the target nerve or that the probe is far enough from non-targeted nerves in order to preserve them from being ablated. The challenge in using electrical stimulation to guide the probe and to interrogate nervous circuitry is the lack of a suitable outcome measure. For example, sensory stimulation relies on patient feedback and can only be used in cases when the patient is stable and alert. Further, the use of sensory stimulation has been shown to be ineffective at guiding the ablative probe to the target nerve and also leads to poor treatment outcomes. Motor stimulation is equally ineffective, and is again burdened by the lack of a suitable outcome measure. Observations made in humans and results from pre-clinical studies show that visual inspection of the lower back muscle twitch or electromyographic signals recorded from the skin's surface are non-descriptive and cannot be used to indicate the electrical proximity of the probe to the target nerve, nor to the nearby non-targeted nerves. In light of the problems discussed above, the present inventors have found that recordings of electromyography signals recorded from specific muscle fascicles (e.g. medial, intermediate and lateral multifidus muscles) indeed have the resolution to monitor target and non-target nerves, to better enable the RF ablation procedure.

As such, there is an unmet need for a system and method capable of enabling the placement of the RF ablation probe in electrical proximity to the target nerve, preserving non-targeted nerves and tissues by recognizing their location and shielding them from the RF ablation energy, identifying which nerve(s) carry the painful signal(s), and confirming intraoperatively that the target nerve has been lesioned.

SUMMARY OF THE INVENTION

The problems described above are addressed by the present invention, which encompasses methods and systems that monitor for electrical muscle activity during location, stimulation, and/or ablation of a target nerve.

According to one embodiment of the present invention, a system for locating a first target nerve associated with a facet joint via nerve stimulation and monitoring of electrical muscle activity in a multifidus muscle adjacent the first target nerve is provided. The multifidus muscle includes a medial fascicle, an intermediate fascicle, and a lateral fascicle, and the system includes a first probe, a first recording electrode, a signal generator, and a controller. The first probe includes an insulated shaft and a first probe electrode located at a distal end of the shaft, wherein the first probe is housed within a first cannula. The first recording electrode monitors electrical muscle activity in the medial fascicle of the multifidus muscle and is configured for placement in the medial fascicle of the multifidus muscle. The controller is coupled to the first probe electrode and the first recording electrode, wherein the controller delivers a first nerve stimulation from the signal generator to the first target nerve via the first probe electrode, wherein the controller monitors electrical muscle activity in the medial fascicle via the first recording electrode, wherein proximity of the first probe to the first target nerve is determined by the electrical muscle activity in the medial fascicle elicited as a result of the first nerve stimulation, and wherein the controller provides feedback to a user to guide placement of the first probe adjacent the first target nerve.

In one particular embodiment, the system includes one or more additional recording electrodes for monitoring electrical muscle activity in the intermediate fascicle, the lateral fascicle, other paraspinal muscles surrounding the multifidus muscle, or a combination thereof, wherein the one or more additional recording electrodes are configured for placement in the intermediate fascicle, the lateral fascicle, paraspinal muscles surrounding the multifidus muscle, or a combination thereof.

For instance, the controller can be configured to monitor for electrical muscle activity in the intermediate fascicle, the lateral fascicle, paraspinal muscles surrounding the multifidus muscle, or a combination thereof, wherein proximity of the first probe to the first target nerve is determined by the electrical muscle activity elicited in the intermediate fascicle, the lateral fascicle, paraspinal muscles surrounding the multifidus muscle, or a combination thereof as a result of the first nerve stimulation, where the controller provides feedback to a user to guide placement of the first probe adjacent the first target nerve and prevent placement of the first probe adjacent non-target tissue.

The system can also be configured for locating a second target nerve located at a level cephalad to a level of the first target nerve, wherein the controller is configured to deliver a second nerve stimulation to the second target nerve via the first probe electrode, further wherein the controller is configured to monitor for electrical muscle activity in the intermediate fascicle, the lateral fascicle, paraspinal muscles surrounding the multifidus muscle, or a combination thereof via the one or more additional recording electrodes, wherein proximity of the first probe to the second target nerve is determined by the electrical muscle activity in the intermediate fascicle, the lateral fascicle, paraspinal muscles surrounding the multifidus muscle, or a combination thereof elicited as a result of the second nerve stimulation, where the controller provides feedback to a user to guide placement of the first probe adjacent the second target nerve and to prevent placement of the first probe adjacent non-target tissue.

Further, the system can include a second probe that includes an insulated shaft and a second probe electrode located at a distal end of the shaft, wherein the second probe is housed within a second cannula, wherein the system is configured for locating a second target nerve located at a level cephalad to a level of the first target nerve, wherein the controller is configured to deliver a second nerve stimulation to the second target nerve via the second probe electrode, further wherein the controller is configured to monitor for electrical muscle activity in the intermediate fascicle, the lateral fascicle, paraspinal muscles surrounding the multifidus muscle, or a combination thereof via the one or more additional recording electrodes, wherein proximity of the second probe to the second target nerve is determined by the electrical muscle activity in the intermediate fascicle, the lateral fascicle, paraspinal muscles surrounding the multifidus muscle, or a combination thereof elicited as a result of the second nerve stimulation, where the controller provides feedback to a user to guide placement of the second probe adjacent the second target nerve and to prevent placement of the second probe adjacent non-target tissue.

In another embodiment, the first recording electrode can have a monopolar configuration, a bipolar configuration, or a multipolar configuration.

In still another embodiment, the first recording electrode can be disposed on a needle.

In yet another embodiment, the first recording electrode can be disposed on the first probe at the distal end of the shaft, wherein the first recording electrode includes a tine extending from the shaft.

In an additional embodiment, the one or more additional recording electrodes can have a monopolar configuration, a bipolar configuration, or a multipolar configuration.

In one more embodiment, the one or more additional recording electrodes can be disposed on a needle.

In one particular embodiment, the one or more additional recording electrodes can be disposed on an outer surface of the first cannula.

In another embodiment, the first probe electrode can have a monopolar configuration, a bipolar configuration, or a multipolar configuration.

Further, the first probe electrode can include an array of independent channels for nerve stimulation, nerve ablation, or a combination thereof, each channel having an axial dimension and a radial dimension, wherein each channel is adapted to be separately energized.

In still another embodiment, monitoring electrical muscle activity in the medial fascicle can include measuring changes in electrical muscle activity latency, burst area, amplitude, or a combination thereof. When the first nerve stimulation is applied at a constant stimulation intensity, a decrease in latency, an increase in burst area, an increase in amplitude, or a combination thereof can indicate that the first probe is in closer proximity to the first target nerve, while an increase in latency, a decrease in burst area, a decrease in amplitude, or a combination thereof can indicate that the first probe is farther away in proximity to the target nerve. On the other hand, when the latency, burst area, amplitude, or a combination thereof are held constant, a decrease in the first nerve stimulation intensity can indicate that the first probe is in closer proximity to the first target nerve and an increase in the first nerve stimulation intensity can indicate that the first probe is farther away in proximity to the first target nerve.

In yet another embodiment, the system can determine if the first target nerve carries a pain signal by monitoring for changes in electrical muscle activity in the medial fascicle elicited as a result of a third nerve stimulation. Further, determining that the first target nerve carries the pain signal can include measuring electrical muscle activity latency, burst area, amplitude, or a combination thereof.

In an additional embodiment, the first probe can include a sharp tip at the distal end for navigating through tissue.

In one more embodiment, the first probe can be configured to form a lesion on the first target nerve by delivery of radiofrequency ablation energy. Further, the system can confirm successful formation of the lesion via the recording electrode, one or more additional recording electrodes, or a combination thereof. The one or more additional recording electrodes can monitor electrical muscle activity in the medial fascicle, the intermediate fascicle, the lateral fascicle, paraspinal muscles surrounding the multifidus muscle, or a combination thereof, wherein the one or more additional recording electrodes are configured for placement in the medial fascicle, the intermediate fascicle, the lateral fascicle, paraspinal muscles surrounding the multifidus muscle, or a combination thereof.

The system can confirm successful formation of the lesion via a fourth nerve stimulation and one or more stimulating electrodes. The one or more stimulating electrodes can be disposed on the probe, an outer surface of the first cannula, on a surface of skin, on a percutaneous needle, or a combination thereof. Further, the controller can provide feedback to the user indicating successful formation of the lesion on the first target nerve based on a predefined level of change in electrical muscle activity. For instance, delivery of radiofrequency energy from the first probe can be discontinued upon confirming successful formation of the lesion on the first target nerve.

In one particular embodiment, the first target nerve can be a medial nerve branch of a dorsal ramus, where electrical muscle activity in the medial fascicle of the multifidus muscle is monitored. However, it is to be understood that electrical muscle activity in intermediate and lateral fascicles of the multifidus muscle as well as electrical muscle activity the longissimus muscle and/or the iliocostalis muscle can also be monitored, respectively, in order to stimulate the first target nerve and/or other target nerves such as the intermediate nerve branch of the dorsal ramus and/or the lateral nerve branch of the dorsal ramus or a target nerve located at a level cephalad to a level of the first target nerve.

Further, the system can be configured to generate a sound or visual indicator to indicate electrical proximity to the first target nerve.

In accordance with another embodiment of the present invention, a method for locating a first target nerve associated with a facet joint via nerve stimulation and monitoring of electrical muscle activity in a multifidus muscle adjacent the first target nerve is provided, where the multifidus muscle includes a medial fascicle, an intermediate fascicle, and a lateral fascicle. The method includes inserting a first recording electrode for monitoring electrical muscle activity in the medial fascicle of the multifidus muscle; positioning a first probe comprising an insulated shaft and a first probe electrode located at a distal end of the shaft near the first target nerve, wherein the first probe is housed within a first cannula; generating a first nerve stimulation from a signal generator; delivering the first nerve stimulation to the first target nerve via the first probe electrode; monitoring electrical muscle activity in the medial fascicle of the multifidus muscle via the first recording electrode; and guiding placement of the first probe adjacent the first target nerve based on the electrical muscle activity elicited in the medial fascicle of the multifidus muscle.

In one particular embodiment, the method can further include inserting one or more additional recording electrodes for monitoring electrical muscle activity in the intermediate fascicle, the lateral fascicle, paraspinal muscles surrounding the multifidus muscle, or a combination thereof; and monitoring electrical muscle activity in the intermediate fascicle, the lateral fascicle, paraspinal muscles surrounding the multifidus muscle, or a combination thereof via the one or more additional recording electrodes.

In another embodiment, the method can include guiding placement of the first probe adjacent the first target nerve based on the electrical muscle activity elicited in the intermediate fascicle, the lateral fascicle, paraspinal muscles surrounding the multifidus muscle, or a combination thereof; and preventing placement of the first probe adjacent non-target tissue.

In still another embodiment, the method can include locating a second target nerve located at a level cephalad to a level of the first target nerve, wherein the method further includes positioning the first probe near the second target nerve; generating a second nerve stimulation from the signal generator; delivering the second nerve stimulation to the second target nerve via the first probe electrode; monitoring electrical muscle activity in the intermediate fascicle, the lateral fascicle, paraspinal muscles surrounding the multifidus muscle, or a combination thereof via the one or more additional recording electrodes; and guiding placement of the first probe adjacent the second target nerve and preventing placement of the first probe adjacent non-target tissue based on the electrical muscle activity elicited in the intermediate fascicle, the lateral fascicle, paraspinal muscles surrounding the multifidus muscle, or a combination thereof.

In yet another embodiment, the method can include locating a second target nerve located at a level cephalad to a level of the first target nerve, wherein the method further includes positioning a second probe comprising an insulated shaft and a second probe electrode located at a distal end of the shaft near the second target nerve, wherein the second probe is housed within a second cannula; generating a second nerve stimulation from the signal generator; delivering the second nerve stimulation to the second target nerve via the second probe electrode; monitoring electrical muscle activity in the intermediate fascicle, the lateral fascicle, paraspinal muscles surrounding the multifidus muscle, or a combination thereof via the one or more additional recording electrodes; and guiding placement of the second probe adjacent the second target nerve and preventing placement of the second probe adjacent non-target tissue based on the electrical muscle activity elicited in the intermediate fascicle, the lateral fascicle, paraspinal muscles surrounding the multifidus muscle, or a combination thereof.

In an additional embodiment, the first recording electrode can have a monopolar configuration, a bipolar configuration, or a multipolar configuration.

In one more embodiment, the first recording electrode can be disposed on a needle.

In one particular embodiment, the first recording electrode can be disposed on the first probe at the distal end of the shaft, wherein the first recording electrode includes a tine extending from the shaft.

In another embodiment, the one or more additional recording electrodes can have a monopolar configuration, a bipolar configuration, or a multipolar configuration.

In still another embodiment, the one or more additional recording electrodes can be disposed on an outer surface of the first cannula.

In yet another embodiment, the first probe electrode can include an array of independent channels for nerve stimulation, nerve ablation, or a combination thereof, each channel having an axial dimension and a radial dimension, wherein each channel is adapted to be separately energized. In such an embodiment, the method can further include selectively activating one or more of the independent channels in the array to direct nerve stimulation energy to the first target nerve. For instance, selectively activating one or more of the independent channels in the array can include delivering a low-level nerve stimulation from each of the one or more independent channels in the array and determining which of the one or more independent channels in the array to activate based on changes in electrical muscle activity latency, burst area, amplitude, or a combination thereof in the medial fascicle as a result of the low-level nerve stimulation.

In an additional embodiment, monitoring electrical muscle activity in the medial fascicle of the multifidus muscle can include measuring changes in electrical muscle activity latency, burst area, amplitude, or a combination thereof. Further, when the first nerve stimulation is applied at a constant stimulation intensity, a decrease in latency, an increase in burst area, an increase in amplitude, or a combination thereof can indicate that the first probe is in closer proximity to the first target nerve. Meanwhile, when the latency, burst area, amplitude, or a combination thereof are maintained at a constant level, a decrease in the first nerve stimulation intensity can indicate that the first probe is in closer proximity to the first target nerve.

In one more embodiment, the method can include delivering a third nerve stimulation; and monitoring for changes in electrical muscle activity in the medial fascicle elicited as a result of the third nerve stimulation to determine if the first target nerve carries the pain signal. Further, determining that the first target nerve carries the pain signal can include measuring electrical muscle activity latency, burst area, amplitude, or a combination thereof.

In one particular embodiment, the first probe can include a sharp tip at the distal end for navigating through tissue.

In another embodiment, the method can include forming a lesion on the first target nerve by delivering radiofrequency ablation energy from the first probe. Further, successful formation of the lesion can be confirmed via the recording electrode, one or more additional recording electrodes, or a combination thereof. In addition, the one or more recording electrodes can monitor electrical muscle activity in the medial fascicle, the intermediate fascicle, the lateral fascicle, paraspinal muscles surrounding the multifidus muscle, or a combination thereof, wherein the one or more additional recording electrodes are configured for placement in the medial fascicle, the intermediate fascicle, the lateral fascicle, paraspinal muscles surrounding the multifidus muscle, or a combination thereof.

In still another embodiment, the method can include confirming successful formation of the lesion on the first target nerve via a fourth nerve stimulation and one or more stimulating electrodes. The one or more stimulating electrodes can be disposed on a probe, an outer surface of the first cannula, on a surface of skin, on a percutaneous needle, or a combination thereof. In addition, successful formation of the lesion on the first target nerve can be indicated by a predefined level of change in electrical muscle activity. In addition, delivering radiofrequency ablation energy from the first probe can be discontinued upon confirming successful formation of the lesion on the first target nerve.

In still another embodiment, the first target nerve can be a medial nerve branch of a dorsal ramus, where electrical muscle activity in the medial fascicle of the multifidus muscle is monitored. However, it is to be understood that electrical muscle activity in intermediate and lateral fascicles of the multifidus muscle as well as electrical muscle activity in the longissimus muscle and/or the iliocostalis muscle can also be monitored, respectively, in order to stimulate the first target nerve and/or other target nerves such as the intermediate nerve branch of the dorsal ramus and/or the lateral nerve branch of the dorsal ramus or a target nerve located at a level cephalad to a level of the first target nerve.

In addition, the method can include generating a sound or visual indicator to indicate electrical proximity to the first target nerve.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIGS. 12A, 12B, and 12C illustrate partial view of an RF ablation probe near its active tip that can be used in conjunction with the EMG subsystem of FIG. 1 and the system of FIG. 4.

FIGS. 13A, 13B, and 13C illustrate partial view of an RF ablation probe near its active tip that can be used in conjunction with the EMG subsystem of FIG. 1 and the system of FIG. 4.

FIG. 14 is a perspective side view of a cannula or introducer and RF ablation probe that can be used in conjunction with the EMG subsystem of FIG. 1 and the system of FIG. 4.

Figure 1:
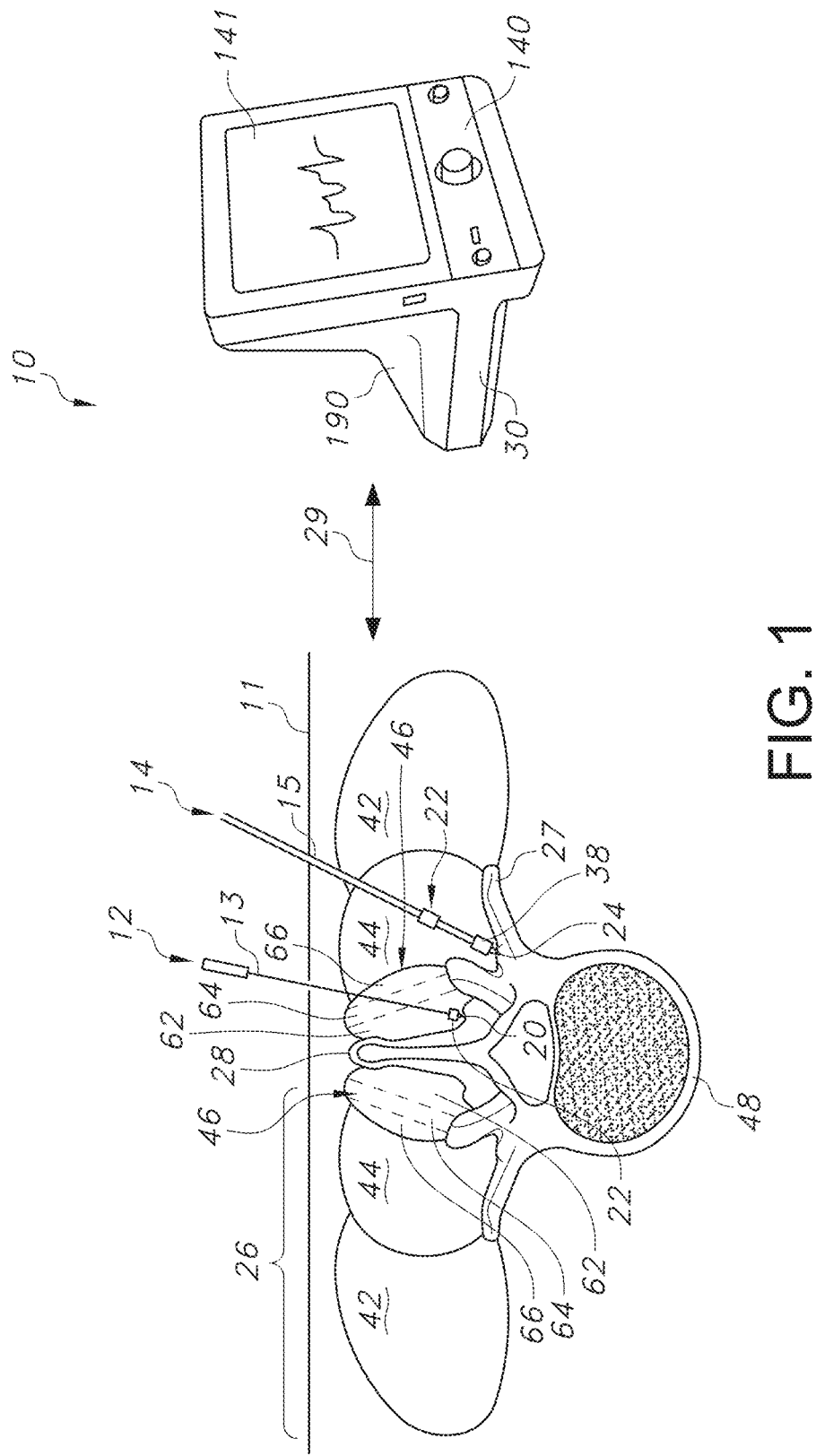
FIG. 1 illustrates an exemplary electromyography (EMG) subsystem as contemplated by the present invention, where the system enables accurate placement of a radiofrequency ablation (RF) probe so that a target nerve can be ablated, allows for confirmation that a lesion has been formed during an RF ablation procedure, and ensures nearby non-target nerve tissues are preserved.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a system and method for using electrical muscle activity as measured via electromyography (EMG) to locate a target nerve and position an RF ablation probe in electrical proximity to the target nerve for subsequent stimulation and/or ablation of the target nerve. The method and system also contemplate the ability to preserve non-target nerves and tissues by recognizing their location and shielding the non-target nerves and tissue from ablative energy delivered by the RF ablation probe to the target nerve or painful circuitry. The method and system can also be used to determine if the target nerve is associated with pain by determining if it carries a pain signal. Further, the method and system can be used intraoperatively during an RF ablation procedure to confirm successful lesioning of the target nerve.

More specifically, a system and method for locating a target nerve associated with a facet joint via nerve stimulation and monitoring of electrical muscle activity in a multifidus muscle adjacent the target nerve are described. The system includes a probe housed within a cannula and comprising a probe electrode; a recording electrode for monitoring electrical muscle activity in a medial fascicle of the multifidus muscle; a signal generator; and a controller coupled to the probe electrode and recording electrode. The controller delivers a nerve stimulation from the signal generator to the nerve via the probe electrode and monitors electrical muscle activity in the medial fascicle via the recording electrode. The probe's proximity to the nerve is determined by the electrical muscle activity in the medial fascicle elicited as a result of the nerve stimulation, where the controller provides feedback to a user to guide placement of the probe adjacent the nerve.

For instance, the monitoring of electrical muscle activity in the medial fascicle of the multifidus muscle can include measuring changes in electrical muscle activity latency, burst area, amplitude, or a combination thereof. When the nerve stimulation is applied at a constant stimulation intensity, a decrease in latency, an increase in burst area, an increase in amplitude, or a combination thereof can indicate that the probe is in closer proximity to the target nerve, while an increase in latency, a decrease in burst area, a decrease in amplitude, or a combination thereof can indicate that the first probe is farther away in proximity to the target nerve. Meanwhile, if the latency, burst area, amplitude, or a combination thereof are held constant, then a decrease in the nerve stimulation intensity can indicate that the first probe is in closer proximity to the first target nerve. On the other hand, an increase in the first nerve stimulation intensity can indicate that the first probe is farther away in proximity to the first target nerve.

Further, the probe electrode can include an array of independent channels for nerve stimulation, nerve ablation, or a combination thereof, where each independent channel is adapted to be separately energized, which provides the system with the ability to preserve non-target nerves and tissues by shielding the non-target nerves and tissue from ablative energy delivered by the RF ablation probe to the target nerve or painful circuitry. The system can also determine if the target nerve carries a pain signal by monitoring for changes in electrical muscle activity in the medial fascicle elicited as a result of an additional nerve stimulation and analyzing changes in electrical muscle activity latency, burst area, amplitude, or a combination thereof.

Moreover, it is to be understood that the system can be used to locate one or more additional target nerves (e.g., the medial nerve branch, the intermediate nerve branch, and the lateral nerve branch extending from the dorsal ramus) at a given spinal level or at one or two levels cephalad by recording electrical muscle activity in the different fascicles of the multifidus muscle as well as the other paraspinal muscles (e.g., longissimus muscle and iliocostalis muscle) and by using the same probe and EMG recording electrode or one or more additional probes and one or more additional stimulating electrodes.

For example, in one particular embodiment, three target nerves can be located at three different neurological levels by monitoring and measuring the electrical muscle activity in three different segments of a muscle. Then, it can be determined if each of the three target nerves is associated with painful circuitry, and the three target nerves can be stimulated, ablated, or a combination thereof with an three different probe electrodes based on the monitored electrical muscle activity. Next, immediately after ablation, the electrical muscle activity associated with each of the three target nerves can be monitored to determine if the lesion successfully ablated the target nerves.

Specifically, the three target nerves can be the medial nerve branch extending from a dorsal ramus at a first neurological level, a medial nerve branch extending from the dorsal ramus at a second neurological level that is one level cephalad to the first neurological level, and a medial nerve branch extending from the dorsal ramus at a third neurological level that is two levels cephalad to the first neurological level. Further, the electrical muscle activity associated with the medial nerve branch at the first neurological level can be monitored via one or more recording electrodes present in the medial fascicle of the multifidus muscle at the first neurological level. Meanwhile, the electrical muscle activity associated with the medial nerve branch at the second neurological level can be monitored via one or more recording electrodes present in the intermediate fascicle of the multifidus muscle at the first neurological level, and the electrical muscle activity associated with the medial nerve branch at the third neurological level can be monitored via one or more recording electrodes present in the lateral fascicle of the multifidus muscle at the first neurological level. However, it is also to be understood that any number of other target nerves (e.g., the intermediate and lateral nerve branches extending of a dorsal ramus) can be monitored and treated, where the additional target nerves can be located at a neurological level caudal to the neurological level of the first target nerve. Further, it is also to be understood that the electrical muscle activity associated with non-target nerves can be monitored in order to avoid delivering radiofrequency ablation energy to the non-target nerves. For instance, when the target nerve is a medial nerve branch, electrical muscle activity in the longissimus muscle and iliocostalis muscle can be monitored in order to avoid delivering stimulation energy to the intermediate nerve branch and the lateral nerve branch. The various components of the system and method contemplated by the present invention are discussed in more detail below.

Referring to FIG. 1, the present invention includes an EMG subsystem 10 that is utilized to identify a target nerve that is a source of pain, assist in accurate placement of an RF stimulation and ablation probe 16 (see FIG. 4) to destroy (e.g., lesion) the target nerve at a facet joint near a vertebra 48 having a transverse process 27 and a spinous process 28, where the facet joint is suspected of being a source of the pain. The EMG subsystem 10 can also be used to preserve non-target nerves and tissues, and confirm that a lesion of the target nerve has been successfully formed to alleviate the pain experienced by the patient. The EMG subsystem 10 can include one or more EMG recording electrodes 22, a muscle activity monitor 190, a hardware interface 29 that can include cables, signal conditioners, amplifiers, and acquisition equipment to capture one or multiple channels of recorded signals, control software 30 to process, analyze, and report recorded EMG signals and to control stimulation, and a user interface 140 that includes a display 141 to observe the recorded EMG waveforms. Leads can extend from the recording electrodes described above and can be connected to a cable that is standalone, or is embodied within the cable that connects to the RF ablation probe 16. The cable may have single or multiple channels to accept EMG inputs and can pass to signal conditioners, filters, amplifiers, and acquisition equipment. Importantly, the cable is shielded and the amplifier is isolated. The signal may be conditioned to accommodate for DC-offset as well as electrical and mechanical noise. Meanwhile, the software 30 can be present on the pulse generator 130 (see FIG. 4) used for stimulation and ablation via the RF ablation probe 16 or can be present on a standalone computer. The software 30 is configured to control the stimulation paradigm, including electrode selection on bipolar and multipolar stimulation electrodes, delivery times, intensities, and waveforms.

Figure 3:
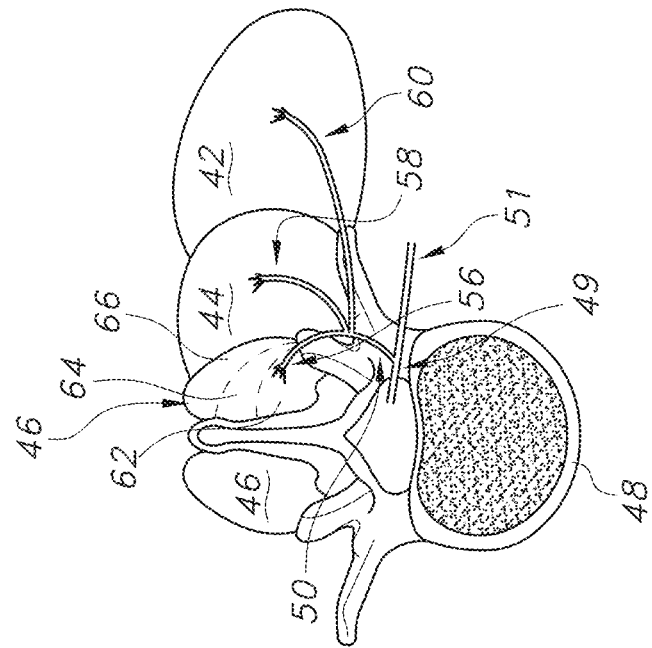
FIG. 3 illustrates a zoomed in view of the paraspinal muscles of FIG. 1 showing the medial fascicle, the intermediate fascicle, and the lateral fascicle of the multifidus muscle, as well as a spinal nerve root, the corresponding dorsal ramus and ventral ramus extending therefrom, as well as the medial nerve branch, intermediate nerve branch, and lateral nerve branch extending from the dorsal ramus.

Referring FIGS. 1-4, the EMG subsystem 10 is a component of a pain management system 100 that includes an RF ablation probe 16 that delivers stimulation energy from a pulse generator 130 to a target nerve. The RF ablation probe 16 can be inserted near the target nerve to be ablated via a cannula 14, where the cannula 14 is inserted through the skin 11 and through the paraspinal muscles 26 until a surface of a bone 27 (e.g., dorsal and medial surface of the transverse process) near the target nerve (e.g., a medial nerve branch 56 of the dorsal ramus 50 as shown in FIG. 3) is reached. The cannula 14 can include the EMG recording electrodes 22, where the EMG recording electrodes 22 are positioned on the cannula 14 so that the EMG recording electrodes 22 are disposed within the particular paraspinal muscle 26 desired to be monitored for EMG activity. However, the EMG recording electrodes 22 can also be placed in the specific multifidus and/or paraspinal muscle 26 via a separate needle 12, as shown in FIG. 1.

For example, when treating facet joint pain transmitted through the medial nerve branch 56 of the dorsal ramus 50 near a vertebra 48 in the lumbar region of the spine such (e.g., an L3 spinal disc), one or more recording electrodes 22 can be placed in the multifidus muscle 46. In particular, the multifidus muscle 46 includes a medial fascicle 62, an intermediate fascicle 64, and a lateral fascicle 66, where placing the EMG recording electrode 22 in the medial fascicle 62 enables for electrical muscle activity of the multifidus muscle 46 associated with the medial nerve branch 56 to be precisely monitored. However, it is also to be understood that additional recording electrodes (not shown in FIG. 1) can be placed within the iliocostalis muscle 42, the longissimus muscle 44, the other fascicles of the multifidus muscle 46, or a combination thereof, to monitor electrical muscle activity associated to provide information about other target nerves (e.g., the intermediate nerve branch 58 extending from the dorsal ramus 50 or the lateral nerve branch 60 extending from the dorsal ramus 50) or to gain additional information regarding the medial nerve branch 56 extending from the dorsal ramus 50, as shown in more detail in FIGS. 2 and 3.

Figure 2:
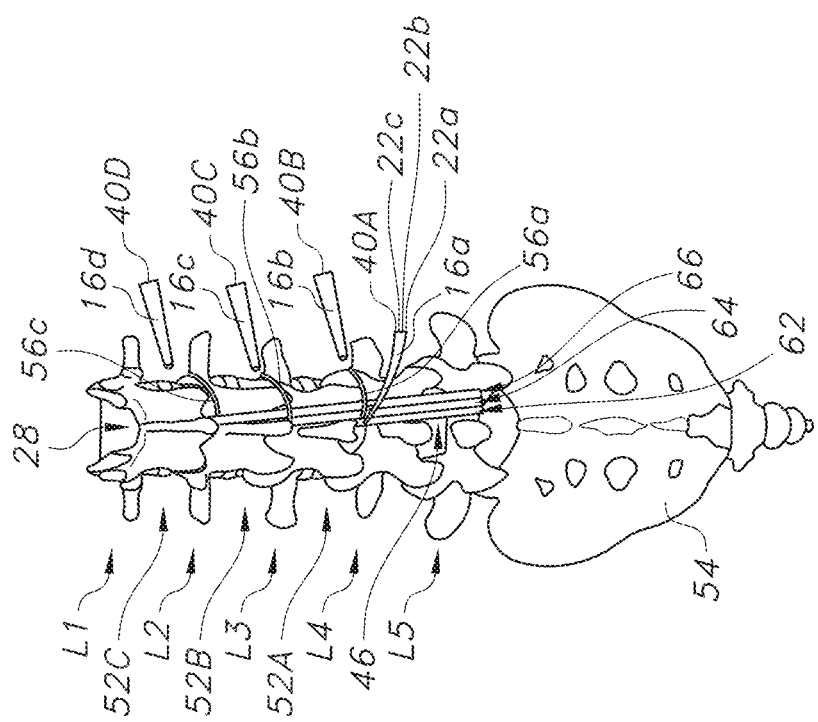
FIG. 2 illustrates the vertebra of FIG. 1 as well as vertebrae at two levels cephalad and two levels caudad to the vertebra of FIG. 1, including multiple stimulation/ablation probes that can be placed near multiple target nerves based on electrical muscle activity monitored by one or more recording electrodes.

Referring specifically to FIG. 2, the vertebra (e.g., L3) of FIG. 1 as well as vertebrae at two levels cephalad (L1 and L2) and two levels caudad (L4 and L5) to L3 are shown above sacrum 54. For example, vertebrae L4 and L3 meet at facet joint 52a, vertebrae L3 and L2 meet at facet joint 52b, and vertebrae L2 and L1 meet at facet joint 52c. As shown, each facet joint 52a, 52b, or 52c is associated with a medial nerve branch 56a, 56b, or 56c extending from a corresponding dorsal ramus (not shown; see FIG. 3 for detail). The medial nerve branch 56a at one neurological level, such as at the L3-L4 facet joint 52a, innervates the medial fascicle 62 of the multifidus muscle 46. However, at one neurological level cephalad (e.g., at the L2-L3 facet joint 52b), the medial nerve branch 56b innervates the intermediate fascicle 64 of the multifidus muscle 46, and at two neurological levels cephalad (e.g., at the L1-L2 facet joint 52c), the medial nerve branch 56c innervates the lateral fascicle 66 of the multifidus muscle 46, as shown. In order to treat facet joint pain transmitted through the medial nerve branches 56a, 56b, and 56c, multiple stimulation/ablation probes 16a, 16b, 16c, and 16d, multiple recording electrodes 22a, 22b, and 22c, and multiple stimulation/ablation electrodes 40a, 40b, 40c, and 40d can be placed as shown.

In one embodiment, probes 16a and 16b can be inserted near the multifidus muscle 46 at facet joint 52a for stimulation and ablation of the medial nerve branch 56a associated with vertebra L4. Stimulation/ablation electrodes 40a and 40b can then be used to stimulate or ablate the medial nerve branch 56a based on electrical muscle activity monitored via recording electrodes 22a, 22b, and 22c. As shown, recording electrode 22a can be placed in the medial fascicle 62 of the multifidus muscle 46, recording electrode 22b can be placed in the intermediate fascicle 64 of the multifidus muscle 46, and recording electrode 22c can be placed in the lateral fascicle 66 of the multifidus muscle 46. The electrical muscle activity recorded from recording electrodes 22a, 22b, and 22c in response to stimulation delivered from stimulation/ablation electrode 40a can then be monitored to determine if the correct target nerve (e.g., the medial nerve branch 56a) has been identified for ablation via probe 16a and/or 16b and stimulation/ablation electrodes 40 and 40b. The electrical muscle activity recorded from recording electrodes 22a, 22b, and 22c can also be used to identify other target nerves such as medial nerve branch 56b and/or medial nerve branch 56c in response to stimulation delivered from stimulation electrodes 16c, and/or 16d. Then probes 16c and 16d can be used to ablate medial nerve branch 56b and medial nerve branch 56c, respectively, via stimulation/ablation electrodes 40c and 40d. Further, although not shown, the electrical muscle activity recorded from recording electrodes in the longissimus muscle and in the iliocostalis muscle can be used to avoid stimulating or ablating the intermediate nerve branch or the lateral nerve branch (e.g., the non-target nerves in the aforementioned scenario).

Next, referring specifically to FIG. 3, the location of various nerve branches with respect to the medial fascicle 62, the intermediate fascicle 64, and the lateral fascicle 66 of multifidus muscle 46, the longissimus muscle 44, and the iliocostalis muscle 42 are shown. Specifically, the spinal nerve root 49 branches into the dorsal ramus 50 and the ventral ramus 51. Then, a medial nerve branch 56, an intermediate nerve branch 58, and a lateral nerve branch 60 extend from the dorsal ramus 50 to the medial fascicle 62 of the multifidus muscle 46, the longissimus muscle 44, and the iliocostalis muscle 42, respectively. As discussed above, the electrical muscle activity of the various fascicles of the multifidus muscle, the longissimus muscle, and the iliocostalis muscle can be monitored in response to stimulation of the various nerve branches in order to guide the probe to the appropriate target nerve for ablation.

Figure 4:
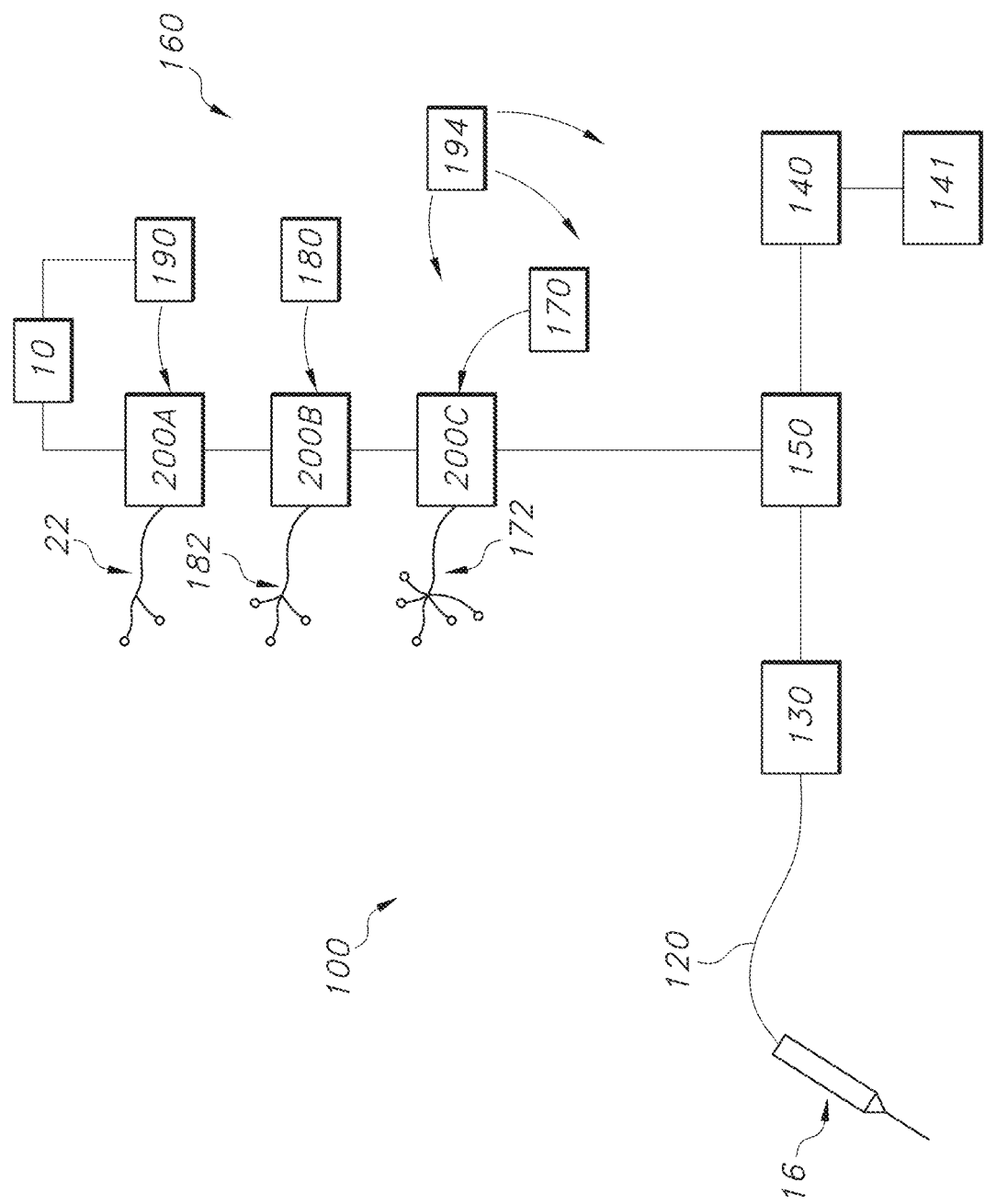
FIG. 4 illustrates a schematic diagram of an exemplary system for ablating target nerve tissue, where the system can include the EMG subsystem of FIG. 1.
Figure 10:
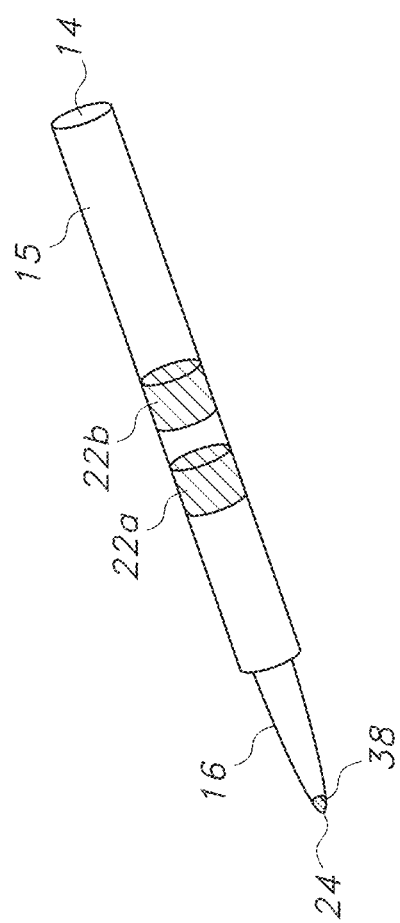
FIG. 10 is a perspective side view of a cannula and RF ablation probe that can be used in conjunction with the EMG subsystem of FIG. 1 and the system of FIG. 4.

Referring now to FIG. 4, one embodiment of the pain management system 100 utilizing the EMG subsystem 10 discussed above with respect to FIGS. 1-3 is shown in more detail. The pain management system 100 can include multiple devices to control and deliver predetermined electrical pulses at predetermined voltages, frequencies, amplitudes (currents), etc. to one or more target nerve(s). As shown in FIG. 4, the pain management system 100 includes a probe 16 that is connected by an electrical lead 120 to the rest of the system 100, which includes a pulse generator 130, a user interface 140, a display 141, and a controller 150. The probe 16 can be a percutaneous probe or any other suitable probe, which can be inserted beneath a surface of skin using cannula 14 as shown in FIGS. 1, 10, and 14. The system 100 also includes a patient monitor system 160, and may further include an isolated power system 180. Each component is discussed in more detail below.

Probe

Figure 5:
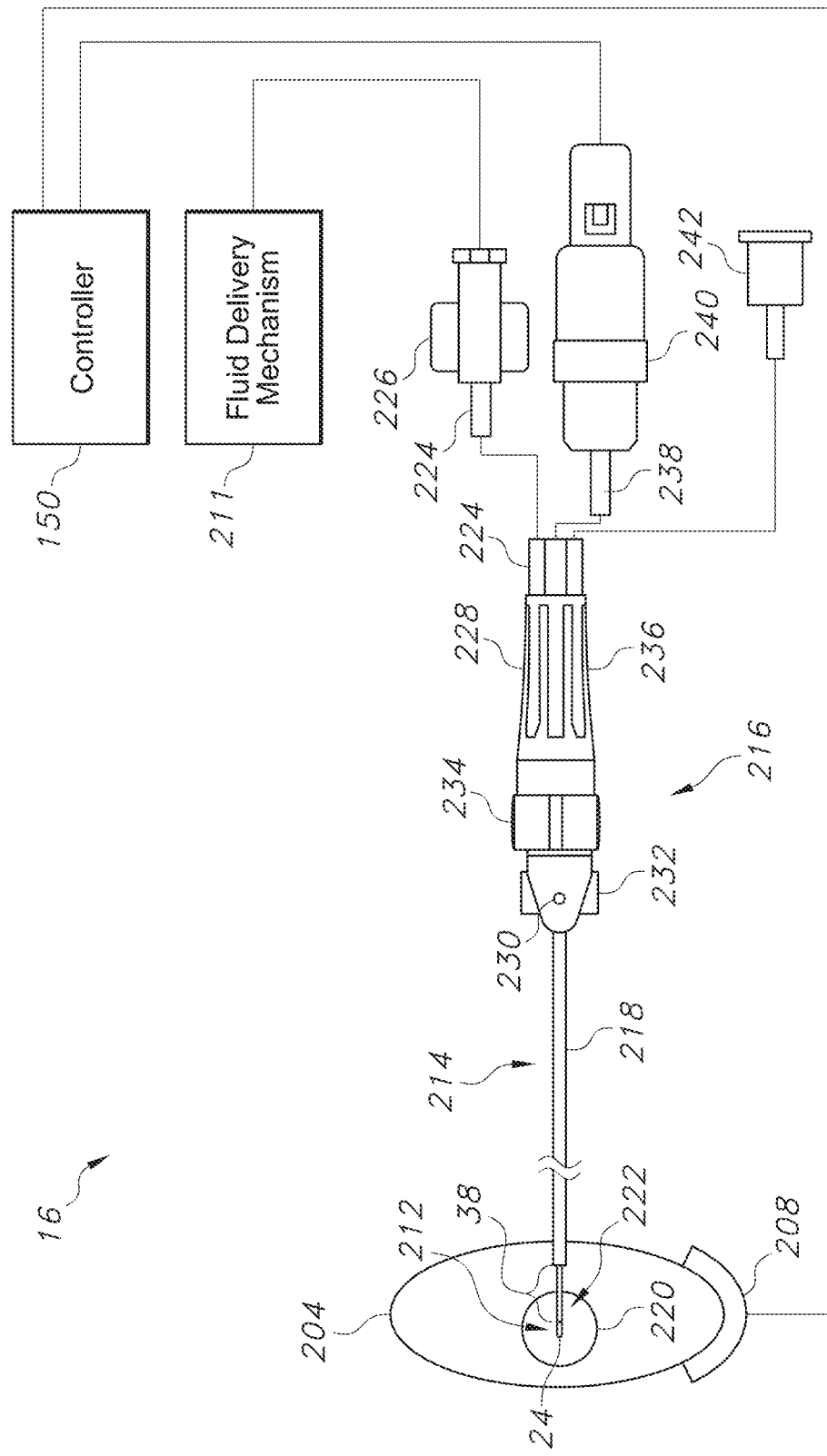
FIG. 5 is a perspective side view of an exemplary probe that can be in the system of FIG. 4 to ablate target nerve tissue.

While any suitable probe 16 can be utilized in the pain management system 100 of the present invention, FIG. 5 shows one example of a suitable percutaneous probe 16 in more detail, where the probe 16 that can be used for stimulating a target nerve 220 is shown. The probe 16 can be coupled to a controller 150 that, among other things, regulates a pulse generator 130 (see FIG. 4), and may also include a return dispersive electrode 208 and a fluid delivery mechanism 211, such as, but not limited to, a syringe, for fluid composition injection. The pulse generator 130 may be controlled to supply energy, such as radiofrequency (RF) energy, to the probe 16, while the controller 150 can also measure temperature feedback from at least one temperature sensor of probe 16. Further, impedance measurement can be carried out between a conductive region 212 of the probe 16 and the return dispersive electrode 208. Impedance measurement may be used during placement of the probe to locate an area of nerve tissue that has specific electrical properties. In addition, the controller 150 may respond to electrical muscle activity such as motor evoked potentials (MEPs) as determined by electromyography (EMG), electrocardiogram (ECG) measurements, electroencephalogram (EEG) measurements, or other means for evaluating a patient's response to a treatment procedure, as discussed in more detail below.

The probe 16 may comprise a conductive shaft 214 and a handle 216. Conductive shaft 214 can have an insulating coating 218 along a major portion of its outer surface, terminating adjacent exposed conductive region 212 at the active tip 24 of the probe, where the conductive region 212 can be referred to as the probe electrode 38. A conductive region 212 can be operable to transmit energy to a target nerve 220 of a neural pathway 204. The conductive region 212 of the probe 16 may aid in the penetration of the probe 16 into, near or around a neural pathway 204 and in the navigation of the probe 16 to a desired target nerve 220. The conductive region 212 can be pointed, sharp, blunt, or open, varying in shape in accordance with the requirements of different procedures. Also, while the length of the conductive region 212 in the first embodiment is between about 2 mm to about 10 mm, this length can vary depending on procedural requirements. The conductive region 212 can optionally be made of medical grade stainless steel, but other conductive biocompatible materials can be used as well. Further, the conductive region 212 can be of varying dimensions and shapes and may be positioned at various locations on a probe 16 utilized in the present invention, such as the active tip 24. Various other embodiments of the active tip 24 of the probe 16, which can include insulated channels in addition to uninsulated channels, are discussed in more detail below with respect to FIGS. 11-14, where it is also to be understood that the probe electrodes 38 can be used for both stimulation and ablation.

Figure 11:
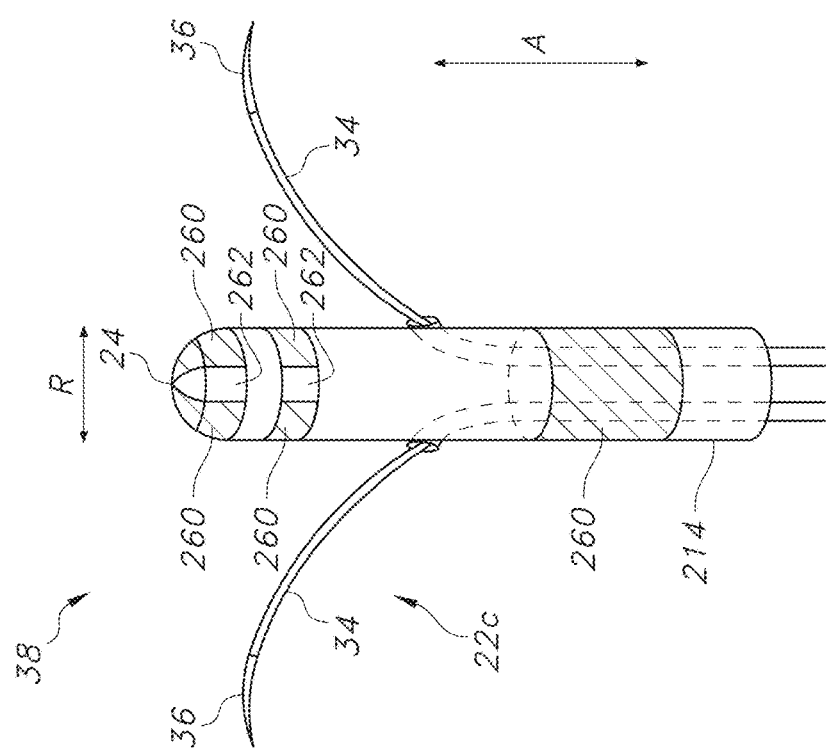
FIG. 11 illustrates a partial view of an RF ablation probe near its active tip that can be used in conjunction with the EMG subsystem of FIG. 1 and the system of FIG. 4.

Turning first to FIG. 11, the probe 16 of FIG. 5 can include a stimulating electrode or probe electrode 38 on its shaft 214 that includes one or more uninsulated (conductive) channels 260 extending in both the axial direction A and radial direction R. The uninsulated channels 260 can be present at the active tip 24 of the probe 16 as well as further down the shaft 214. The probe 16 of FIG. 5 can also include one or more insulated channels 262 extending in both the axial direction A and radial direction R, where the insulated channels 262 can be present at the active tip 24 of the probe 16 as well as further down the shaft 214. The uninsulated channels 260 and insulated channels 262 form an array 33 that can be customized to direct stimulation and/or ablation energy to specific areas of a target nerve in order to preserve non-target tissue, where it is to be understood that each channel in the array 33 can be separately energized and that any combination or pattern of channels can be uninsulated or insulated depending on the particular need.

Figure 12A:
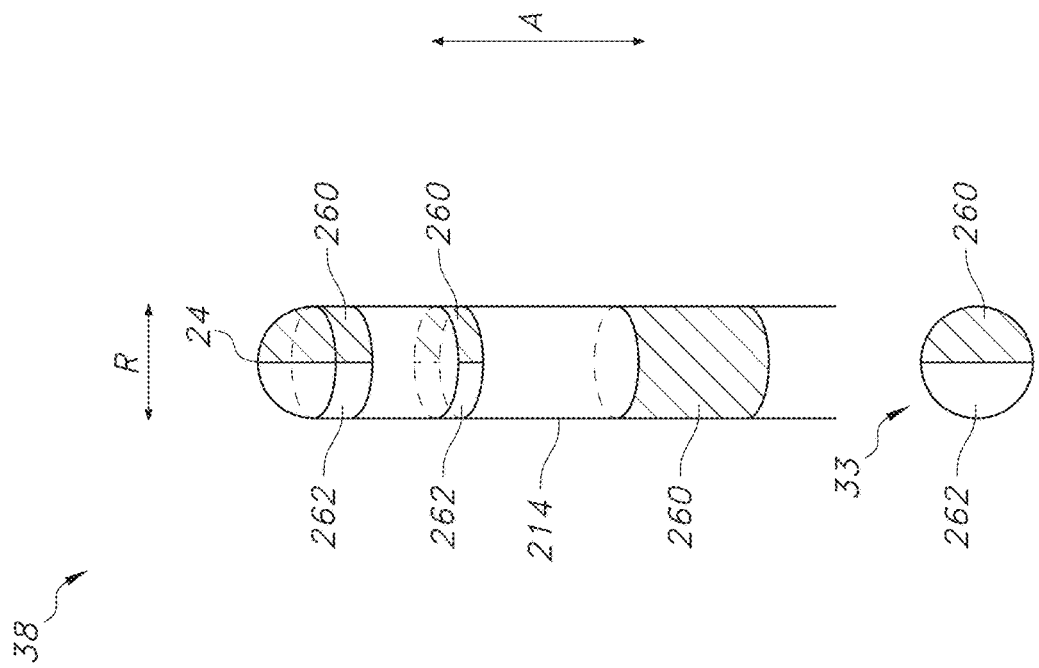

Specific examples of uninsulated channels 260 and insulated channels 262 in the array 33 are shown in FIGS. 12A, 12B, and 12C. FIG. 12A contemplates a stimulation and/or ablation paradigm where the probe electrode 38 has a bipolar arrangement. Specifically, the probe electrode 38 includes an uninsulated channel 260 at the active tip 24 and on the shaft 214, as well as an uninsulated channel 262 at the active tip 24 and on the shaft 214. Meanwhile, FIG. 12B contemplates a stimulation and/or ablation paradigm where the probe electrode 38 has a multipolar arrangement. Specifically, the stimulating electrode 38 includes two uninsulated channels 260 at the active tip 24 and shaft 214, as well as two insulated channels 262 at the active tip 24 and shaft 214. Further, FIG. 12C also contemplates a stimulation paradigm where the probe electrode 38 has a multipolar arrangement. Specifically, the stimulating/ablation probe electrode 38 includes four uninsulated channels 260 and four insulated channels 262. Referring back to FIG. 5, a monopolar arrangement is also contemplated, where a grounding pad (not shown) can be placed on a surface of the patient's skin 11, where a conductive region 212 is present on the active tip 24 and the insulated coating or region 218 is present on the shaft 214 of the probe 16. Meanwhile, FIGS. 13A, 13B, and 13C show various additional channel arrangements for the probe electrode 38 located at the active tip 24 of the probe 16, where the uninsulated channels 260 are disposed on one side of the active tip 24 in various patterns in the axial direction A and radial direction R, while the remainder of the side of the active tip 24 includes an insulated channel 262 and other side of the active tip includes a completely insulated channel 262. For instance, the uninsulated channels 260 can have any desired pattern or shape in order to direct the stimulation energy to the target nerve 220 and away from non-target nerves and tissues. For instance, as shown in FIG. 13A, the uninsulated channels 260 can be in the form of four vertical circles located on one side of the active tip 24, while the remainder of the active tip 24 can be formed of an insulated channel 262. Further, as shown in FIG. 13B, the uninsulated channels 260 can be in the form of a pattern of circles in multiple rows and columns located on one side of the active tip 24, while the remainder of the active tip 24 can be formed of an insulated channel 262. In addition, as shown in FIG. 13C, the uninsulated channels 260 can be in the form of a generally rectangular vertical section surround by a column of circles on each side that are located on one side of the active tip 24, while the remainder of the active tip 24 can be formed of an insulated channel 262. It should also be understood that any other suitable shape or pattern can be used for the uninsulated channels 260, such as circular, square, triangular, etc. Further, it should be understood that the probe electrodes 38 of FIGS. 13A-13C can include uninsulated channel 260 that are present further down the shaft 214 from the active tip 24. Additionally, referring to FIG. 14, it should be understood that additional stimulating electrode(s) 40a and 40b can be located on the cannula 14 used to insert and guide the active tip 24 of the probe 16 to the target nerve 220 and to stimulate one or more paraspinal muscles, such as the longissimus muscle, to monitor the continuity of the target nerve before and after ablation.

Referring back to FIG. 5, in one embodiment, the shaft 214 and conductive region 212 of the probe 16 can be made from a conductive material, for example, stainless steel. Meanwhile, the insulating coating 218 can be made of any type of insulating material, including, but not limited to, polyethylene terephthalate (PET), to prevent the shaft 214 from delivering high frequency electrical current to tissue surrounding the shaft 214. Further, the shaft 214 can have at least one aperture 222 in some embodiments, through which a treatment composition can be administered and exit from the probe 16.

The conductive shaft 214 of the probe 16 may impart rigidity to the probe 16 to facilitate the maneuvering of the conductive region 212 to reach a target nerve 220 of a neural pathway 204, in which case the shaft 214 may be referred to as being rigid or semi-rigid. In other embodiments, the shaft 214 can be flexible. In one embodiment, the shaft 214 can be hollow along its length, defining a lumen. The shaft 214 can be used to transmit a treatment composition to the conductive region 212 and/or the target nerve 220, as well as to support and enclose any wiring associated with the probe 16. Further, an inner diameter of the shaft 214 can be sufficiently dimensioned to accommodate a stylet or obturator in embodiments with an open tip, in addition to wiring for a temperature sensor associated with the distal end of the shaft 214. In some embodiments, the length of the shaft 214 can vary between about 5 centimeters and about 15 centimeters. It is understood, however, that the length can vary beyond this range according to the location of the target nerve and/or the procedure being performed.

In one embodiment, the handle 216 can include a flexible tube 224 coupled thereto in fluid communication with the lumen of the shaft 214. The flexibility of the tube 224 can allow for greater maneuverability of the probe 16. A proximal end of the flexible tube 224 can be coupled to a fluid delivery interface connection 226. In other embodiments (not shown), the handle 216 may not be necessary and the flexible tube 224 can be coupled directly to shaft 214. The handle 216 can optionally provide a grip 228 to allow a user to more easily manipulate the probe 16. In one embodiment, the handle 216 is manufactured from medical grade injection-moldable plastic or other material that can be sterilized using, for example, ethylene oxide. The handle 216 can also have an aperture marker 230 that is in line with an aperture 222 along the axis of the shaft 214 and which can be used to indicate the orientation of the aperture 222 about the axis of the shaft 214. An aperture marker 230 allows the user to target tissue for the delivery of a treatment composition by indicating the orientation of the aperture 222. The handle 216 can further comprise orientation markings, including first orientation markings 232 to indicate, for example, 180° rotation of the probe 16 about the axis of the shaft 214 and second orientation markings 234 to indicate, for example, 90° rotation of the probe 16 about the axis of the shaft 214. The user can then refer to first and/or second orientation markings 232, 234 to prevent the probe 16 from rotating about the axis of the shaft 214 while the probe 16 is inserted through nerve tissue at or near neural pathway 204, or to rotate the probe 16 about the axis of the shaft 214 to a desired orientation. The first and second orientation markings 232, 234 can be visual indicators, which can be flush with the handle 216, or tactile indicators, which can be textured or raised so that the user can see or feel the markings 232, 234 as the probe 16 is inserted into nerve tissue at or near a neural pathway 204. A proximal end of the handle 216 can also have a strain relief 236 with a grip 228 running from the proximal end to the distal end of the strain relief 236. In FIG. 5, the grip 228 is textured, for example with parallel ridges, to provide points of friction for the user while the probe 16 is rotated about the axis of the shaft 214 and inserted through nerve tissue at or near the neural pathway 204. In this embodiment, the ridges on grip the 228 can also be used to determine an angle of rotation of the apparatus. In one embodiment, the strain relief 236 can have a non-round (non-circular) cross-section, which can be square, triangular, or "toothed" like a mechanical gear. The strain relief 236 can be tapered with a larger distal outer diameter, in order to fit with the handle 216, and a smaller proximal outer diameter, in order to secure the electrical cable 238 and the flexible tubing 224. This taper provides increased grip for the user and reduces slipping of the user's fingers as the probe 16 is advanced into nerve tissue at or near a neural pathway 204. The strain relief 236 can provide a comfortable handle for the user and can conform to a user's gripping preference. In FIG. 3, an electrical cable 238 and flexible tubing 224 extend from the handle 216 and the strain relief 236 in parallel and adjacent each other. Notably, in this embodiment, the electrical cable 238 and the flexible tubing 224 do not extend from the handle 216 perpendicular to one another. This arrangement can provide a comfortable grasp and can enhance the ease of manipulation of the probe 16 during placement, rotation, insertion, delivery of therapy, etc.

In one particular embodiment, electrical energy can be supplied to the conductive region 212 from the controller 150 through the pulse generator 130 (FIG. 4) via an electrical coupling, comprising an electrical connector 240, an electrical cable 238 and the conductive shaft 214. All electrical contacts, except for the conductive region 212, can be isolated from the user by a connector pin housing located in the electrical connector 240. The electrical cable 238 can flexibly couple the controller 150 to the conductive shaft 214, which supplies energy to the conductive region 212 via the pulse generator 130 (FIG. 4). The electrical cable 238 can also relay temperature data back to the controller 150. In one particular embodiment, one conductor in the electrical cable 238 can act as both a thermocouple wire as well as an RF delivery wire. Utilizing a single conductor for both purposes reduces the overall mass of the electrical cable 238 and minimizes the forces and moments applied at the handle 216 during placement of probe in, near or around nerve tissue at a neural pathway 204. It will be understood by a person skilled in the art that separate cables and/or conductors may alternatively be used in conjunction with a temperature sensor.

In addition, a fluid delivery mechanism 211 can be flexibly coupled to a fluid delivery interface connection 226, and through it to the shaft 214 via flexible tubing 224, in order to allow the administration of a treatment composition that can include both diagnostic and therapeutic agents to a region of tissue in a patient's body. Therefore, the probe 16 can be simultaneously connected to the fluid delivery mechanism 211 and the pulse generator 130 (FIG. 4) in order to treat a target nerve 220. The fluid delivery interface connection 226 can include any connector including, but not limited to, a luer type connector, that allows for the flow of fluid from the fluid delivery mechanism 211 to the flexible tubing 224.

In operation, the probe 16 is inserted into an area near a neural pathway 204 such as at a target nerve 220. Proper placement of the probe 16 can be confirmed by applying electrical energy using the conductive region 212 to stimulate the target nerve 220 and observing the resulting electrical muscle activity (e.g., motor evoked potentials or MEPs) via EMG, as discussed in more detail below. An anesthetic fluid or another treatment composition can optionally be administered by actuating the fluid delivery mechanism 211. Apart from pharmacological agents, including anesthetics, the applied treatment composition can include, for example, a fluid that is electrically conductive or a fluid used to heat or cool the tissue if desired. The treatment composition can exit the fluid delivery mechanism 211 and flow through the fluid delivery interface connection 226, the flexible tube 224, and the lumen of the shaft 214 to the conductive region 212 where it exits through the aperture 222. The incorporation of a fluid delivery system into the probe 16 allows fluid delivery mechanism 211 to be preconnected to fluid delivery interface connection 226, which can reduce the likelihood of inadvertent movement of the conductive region 212 by removing the requirement to use and therefore remove a separate apparatus to apply a treatment composition, which would generally result in an adjustment of the position of the conductive region 212. Additionally, the use of the flexible tube 224 can further decrease the forces acting on the handle 216 and the shaft 214 when the fluid delivery mechanism 211 is actuated to administer the treatment composition, for example, when a plunger on a syringe is depressed. Therefore, after stimulation to ensure proper placement of the probe 16, manual manipulation of the probe 16 is minimized and thus the likelihood of shifting the probe 16, and thus the conductive region 212, out of position is decreased. Moreover, the use of a probe 16 with a shaft 214 whose distal end is sharp or pointed allows the probe 16 to be inserted without the need to first insert a separate stylet/needle, thus further reducing the likelihood of positional shifting of the probe 16. In other words, because the probe can have a sharp tip, the probe can act as a stylet so that a separate stylet is not required. However, it is to be understood that a cannula 14 (see FIG. 1) with a separate needle/stylet can also be used and is considered to be within the scope of the invention, where the needle/stylet can be modified so that it can deliver electrical stimulation energy.

After optionally administering a treatment composition, radio frequency (RF) energy can be applied to a target nerve 220 through conductive region 212. A return dispersive electrode 208 is provided to create a closed circuit when the probe 16 is electrically operated in contact with the target nerve 220. Since the fluid delivery mechanism 211 is still connected to the probe 16 during energy delivery, it is to be understood that delivery of treatment composition coincident with the delivery of energy is possible. During nerve stimulation and/or treatment, temperature sensor feedback can be used to automatically control the radiofrequency (RF) energy delivered to the target nerve 220 to help ensure safe operation of the probe 16 via controller the 150. For example, if the body tissue temperature increases rapidly while applying RF energy as measured by the temperature sensor feedback mechanism, RF energy delivery to the target nerve 220 can be suspended or reduced to provide a controlled ramp to the desired set temperature, such as based on which procedure or step is being performed. In this manner, the user does not blindly apply RF energy to the nerve tissue, but is informed in real-time of the effects that RF energy delivery has on tissue temperature.

In some embodiments, as has been previously described, the flexible tube 224 can provide the mechanical slack required to ensure that fluid delivery does not introduce added force to the probe 16. Other treatment tool(s) 242, depending on the procedure, can also be flexibly connected to probe 16. Probe 16 can therefore be provided with pre-formed connectors for these treatment tools that are flexibly coupled to probe the 210.

Figure 6:
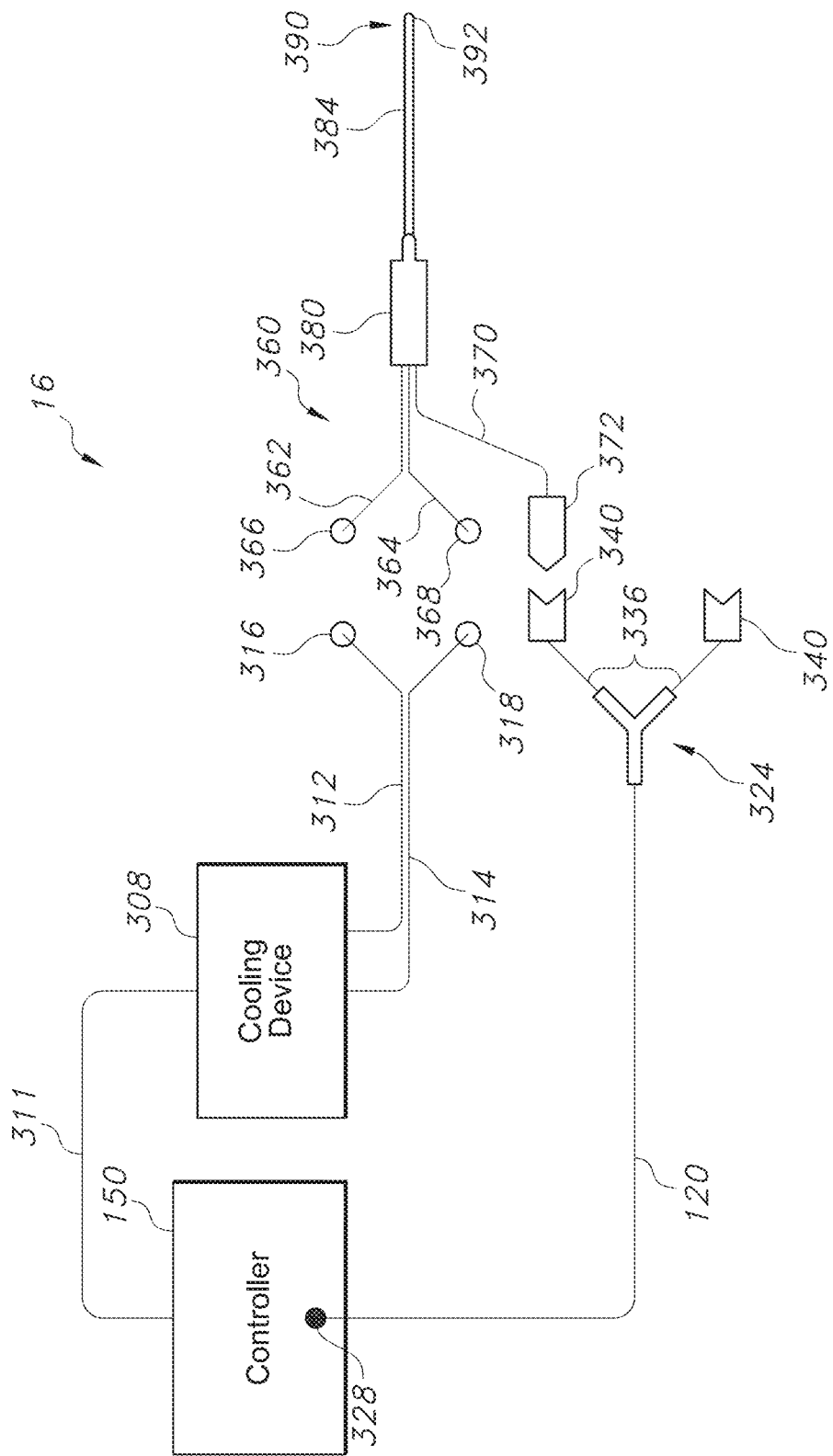
FIG. 6 is perspective side view of another exemplary probe that can be used in the system of FIG. 4 to ablate target nerve tissue.

FIG. 6 shows another embodiment of a suitable percutaneous probe 16. The probe 16 can be coupled to a controller 150 via a lead 120 and to one or more cooling devices 308 via a pump cable 311, one or more proximal cooling supply tubes 312, and one or more proximal cooling return tubes 314. The probe can also be coupled to a pulse generator 130 (FIG. 4) that is controlled by the controller 150. As shown in FIG. 6, a distal region 324 of the lead 120 can include a splitter 330 that can divide the lead 120 into two distal ends 336 such that the probe 16 can be connected to lead 120. Meanwhile, a proximal end 328 of the lead 120 is connected to controller 150. This connection can be permanent, whereby, for example, the proximal end 328 of the lead 120 is embedded within the controller 150, or temporary, where, for example, the proximal end 328 of the lead 120 can be connected to the controller 150 via an electrical connector. The two distal ends 336 of the lead 120 can also terminate in connectors 340 operable to couple to the probe 16 and establish an electrical connection between the probe 16 and the controller 150.

One or more cooling devices 308 can be used and can include any means of reducing a temperature of material located at and proximate to the probe 16. The cooling device 308 can include two peristaltic pumps operable to circulate a fluid from the cooling device 308 through one or more proximal cooling supply tubes 312, the probe 16, one or more proximal cooling return tubes 314 and back to the cooling devices 308. The fluid can be water or any other suitable fluid. In other embodiments, the cooling device 308 can include only one peristaltic pump or one or more electrothermal cooling devices or any other cooling means. The cooling device 308 can be operable to communicate at least uni-directionally, and optionally bi-directionally, with the controller 150. In this way, feedback control can be established between the cooling device 308 and the controller 150. The feedback control involves the controller 150, the probe 16, and the cooling device 308, although any feedback between any two devices is also contemplated. The feedback control can be implemented, for example, in a control module which may be a component of the controller 150. In this embodiment, the controller 150 can be operable to communicate bi-directionally with the probe 16 as well as with the cooling device 308, where bi-directional communication refers to the capability of a device to both receive a signal from and send a signal to another device.

As an example of feedback control, the controller 150 can receive temperature measurements from probe 16. For instance, based on the temperature measurements, the controller 150 can perform some action, such as modulating the power that is sent to the probe 16 from the pulse generator 130 (see FIG. 4). For example, power to the probe 16 could be increased when a temperature measurement is low or decreased when a measurement is high. In some cases, the controller 150 may terminate power to the probe 16. Thus, the controller 150 can receive a signal (e.g., temperature measurement) from the probe 16, determine the appropriate action, and send a signal (e.g., decreased or increased power) back to the probe 16. Alternatively, the controller 150 can send a signal to the one or more cooling devices 308 to either increase or decrease the flow rate or degree of cooling being supplied to the probe 16.

Alternatively, if one or more cooling devices 308 includes one or more peristaltic pumps, the one or more pumps can communicate a fluid flow rate to the controller 150 and may receive communications from the controller 150 instructing the pumps to modulate this flow rate. In some instances, the one or more peristaltic pumps can respond to the controller 150 by changing the flow rate or turning off for a period of time. With the cooling devices 308 are turned off, any temperature sensing elements associated with the probe 16 would not be affected by the cooling fluid, allowing a more precise determination of the surrounding tissue temperature to be made.

In still other embodiments, the one or more cooling devices 308 can reduce the rate of cooling or disengage depending on the distance between the probe 16. For example, when the distance is small enough such that a sufficient current density exists in the region to achieve a desired temperature, little or no cooling may be required. In such an embodiment, energy is preferentially concentrated between first and second energy delivery devices 392 through a region of nerve tissue to be treated, thereby creating a strip lesion. A strip lesion is characterized by an oblong volume of heated tissue that is formed between two electrodes when an active electrode is in close proximity to a return electrode of similar dimensions. This occurs because at a given power, the current density is preferentially concentrated between the electrodes and a rise in temperature results from current density.

One or more cooling devices 308 can also communicate with the generator 130 in order to alert the controller 150 to one or more possible errors and/or anomalies associated with one or more cooling devices 308, such as if cooling flow is impeded or if a lid of the one or more cooling devices 308 is opened. The generator 130 can then act on the error signal by at least one of alerting a user, aborting the procedure, and modifying an action.

In still other embodiments, the controller 150 can communicate with only one of the one or more cooling devices 308 or communication between devices may be unidirectional. For example, the one or more cooling devices 308 can be operable to receive incoming signals from the controller 150 but not to send signals back to the controller 150. In addition to the aforementioned feedback systems, the controller 150 can respond to electromyogram (EMG) measurements, electroencephalography (EEG) measurements, electrocardiogram (ECG) measurements, or some other measure of patient response to a treatment procedure, as discussed below, and then respond accordingly.

As illustrated in FIG. 6, the means of facilitating communication between the one or more cooling devices 308 and the controller 150 can take the form of a pump cable 311 electrically connecting the controller 150 to the one or more cooling devices 308. In other embodiments, the controller 150 and the one or more cooling devices 308 can be connected with an RS-232 cable, a fiber optic cable, a USB cable, a Firewire™ (IEEE1394) cable or other means of electrical coupling. In yet further embodiments, communication between the controller 150 and the one or more cooling devices 308 can be achieved using some other communication protocol including but not limited to infrared, wireless, Bluetooth™ and others and the invention is not limited in this regard.

As illustrated in FIG. 6, the one or more proximal cooling supply tubes 312 can include proximal supply tube connectors 316 at the distal ends of the one or more proximal cooling supply tubes 312. Additionally, the one or more proximal cooling return tubes 314 can include proximal return tube connectors 318 at the distal ends of the one or more proximal cooling return tubes 314.

In one embodiment, the probe 16 can include a proximal region 360, a handle 380, a hollow elongate shaft 384, and a distal tip region 390 including energy delivery devices 392. The proximal region 360 can include a distal cooling supply tube 362, a distal supply tube connector 366, a distal cooling return tube 364, a distal return tube connector 368, a probe assembly cable 370, and a probe cable connector 372. In this embodiment, the distal cooling supply tube 362 and the distal cooling return tube 364 can be flexible to allow for greater maneuverability of the probe 16, but alternate embodiments with rigid tubes are possible.

In one embodiment, the proximal supply tube connector 316 can be operable to interlock with the distal supply tube connector 366 and the proximal return tube connector 318 can be operable to interlock with the distal return tube connector 368. This helps to establish a circuit within which a cooling fluid may flow while maintaining modularity of the probe 16.

In addition, in the embodiment illustrated in FIG. 6, the probe cable connector 372 can be located at a proximal end of the probe assembly cable 370 and can be operable to reversibly couple to one of connectors 340, thus establishing an electrical connection between the controller 150 and the probe 16. The probe assembly cable 370 can include one or more conductors depending on the specific configuration of the probe 16. For example, the probe assembly cable 370 can include five conductors allowing the probe assembly cable 370 to transmit RF current from a pulse generator 130 (FIG. 4), as determined by the controller 150, to the energy delivery device 392, as well as to connect multiple temperature sensing devices to the controller 150 as discussed below.

An energy delivery device 392 can include any means of delivering energy to a region of nerve tissue adjacent distal tip region 390. For example, the energy delivery device 392 can include radio frequency (RF) energy from a pulse generator 130, as discussed below. In one embodiment, the energy delivery device 392 includes an electrode. The active region of the electrode can be 2 millimeters (mm) to 20 mm in length and energy delivered by the electrode can be electrical energy in the form of current in the RF range. In some embodiments, feedback from the controller 150 can automatically adjust the exposed area of the energy delivery device 392 in response to a given measurement such as impedance or temperature. This can be accomplished through the use of an adjustable insulation sleeve associated with the energy delivery device 392. Adjustment of the insulation sleeve can be accomplished through sliding the sleeve proximally or distally along the energy delivery device. The adjustment can be done manually in other embodiments. Alternatively, additional conductive regions can be provided along the distal tip region 390 proximate the energy delivery device 392. In such an embodiment, the extent of nerve impairment, such as the size or shape of a lesion created during an ablation procedure, can be altered by selectively delivering energy through one or more of the additional conductive regions and the energy delivery device 392. Furthermore, one or more energy delivery devices 392 can include any combination of active electrodes and return electrodes, as is well known in the art.

It is to be understood that FIGS. 5-6 and 11-13c are examples of suitable probes that can be utilized. However, other suitable probes can be utilized and are described in U.S. Pat. No. 7,306,596 to Hillier, et al., U.S. Pat. No. 8,187,268 to Godara, et al., and U.S. Pat. No. 8,740,897 to Leung, et al., each of which is hereby incorporated by reference in its entirety. Further, it is also to be understood that more than one probe 16 can be utilized to deliver nerve stimulation to a target nerve, where multiple probes can be connected to multiple channels in the pulse generator (discussed below) for delivery of the nerve stimulation, where each channel can be used for treating a different location or source of pain. For instance, a first probe can be connected to a first channel of a pulse generator to treat a first area of the upper back, a second probe can be connected to a second channel of a pulse generator to treat a second area of the back, a third probe can be connected to a third channel to treat a third area of the back, and a fourth probe can be connected to a fourth channel to treat a fourth area of the back.

Pulse Generator

Returning now to FIG. 4, the probe 16 can be connected to a pulse generator 130 through an electrical lead 120. In one embodiment, the pulse generator 130 can be a bipolar constant current stimulator. One exemplary stimulator is the DIGITIMER DS5 electrical stimulator available from Digitimer Ltd., England. Other constant current and constant voltage pulse generators may be used. Further, as indicated above, the pulse generator can include multiple channels to allow for the treatment of multiple sources or locations of pain, where multiple probes are connected to the multiple channels. In this manner, each source or location of pain can be treated at a different stimulation level if needed because each probe can deliver stimulation from the pulse generator via its own channel. Moreover, multiple chancels can be deposited on each probe to better control the electrical stimulation and ablation fields.

User Interface

The system can also utilize a user interface 140. This user interface 140 can be in the form of a computer that interacts with the controller 150 and can be powered by an isolation system 180, each described herein.

The computer operates software designed to record signals passed from the controller, and to drive the controller's output. Possible software includes Cambridge Electronic Design's (UK) SPIKE program. The software is programmable, can record and analyze electrophysiological signals such as EMG signals, EEG signals, and ECG signals, and can direct the controller to deliver stimulation.

Further, the user interface 140 can include a monitor 141, and the monitor can be configured to show multiple views via a display screen (not shown). For instance, a first view can display information related to probe placement, a second view can display information related to identifying the source of pain, a third view can display information related to treating pain from a target nerve while avoiding non-target nerves and tissues, and a fourth view can display information regarding lesion confirmation.

In addition, the user interface 140 can be configured to generate a sound that indicates electrical proximity to the target nerve. For example, the system 100 may generate a low-pitched sound when the probe's electrical proximity from the target nerve is high, and a high-pitched sound when the probe's electrical proximity to the target nerve is low. This can be enabled by tracking the motor thresholds, or an amount of the motor-threshold of the target nerve/muscle ensemble, where high thresholds would cause low pitched sounds and low thresholds would cause high-pitched sounds. It is also to be understood that the user interface 140 can be configured to generate a visual indicator that indicates electrical proximity to the target nerve. For instance, the display 141 can project a green indicator when the probe 16 is in electrical proximity to the target nerve that can change from yellow to orange to red as the probe 16 is moved farther away from the target nerve.

Patient Monitor System

A patient monitor system 160 can also be used in the system of the present invention. The patient monitoring system can acquire, amplify, and filter physiological signals, and can also output them to the controller 150. Referring to FIGS. 1 and 4, the system includes an electromyography (EMG) subsystem 10 that can include a muscle activity monitor 190 having a display 141, EMG hardware interface 29, and software 30 to collect and display electromyography (EMG) signals. The EMG subsystem 10 also includes EMG recording electrodes 22 that can be coupled with an AC amplifier 200A. The EMG recording electrodes 22 can be present on a needle 12, a cannula 14 used during placement of the RF ablation probe 16, or both.

Regardless of the particular configuration used for the EMG recording electrode(s), one or multiple electrodes can be inserted into muscles to record stimulus-elicited motor evoked potentials as mentioned above. The chosen muscles are dependent on the RF ablation procedure and functional anatomy. For example, during RF ablation procedures to lesion the medial nerve branch of a dorsal ramus in the lumbar spine, electrodes may be placed in the multifidus muscle at the spinal level ipsilateral and contralateral to the ablation site, as well as in multifidus muscles at more cephalad and caudal levels. Additionally, electrodes may be placed in the larger muscles, such as the longissimus and iliocostalis muscles, and again, ipsilateral and contralateral to the ablative site. The electrodes may be of any impedance and of any recording fashion (e.g., monopolar, bipolar, multipolar, concentric, etc.) and may include active, inactive, reference, and grounding electrodes. The reference and grounding electrodes may be applied to the patient's skin, while the active and inactive electrodes may exist at the tip of a needle electrode or along its shaft or on the shaft of a cannula used to insert the RF ablation probe.

Figure 9:
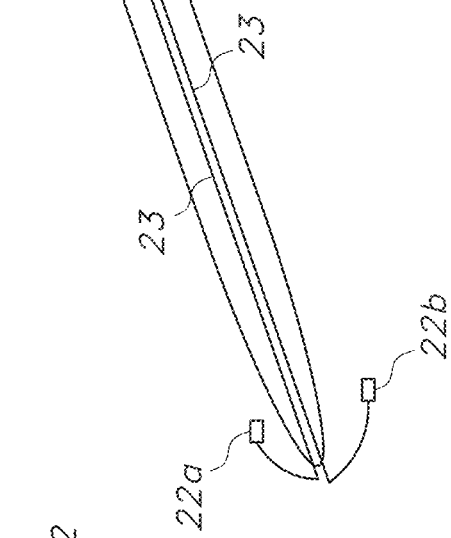
FIG. 9 is perspective side view of another needle that can be used in conjunction with the EMG subsystem of FIG. 1 and the system of FIG. 4.
Figure 8:
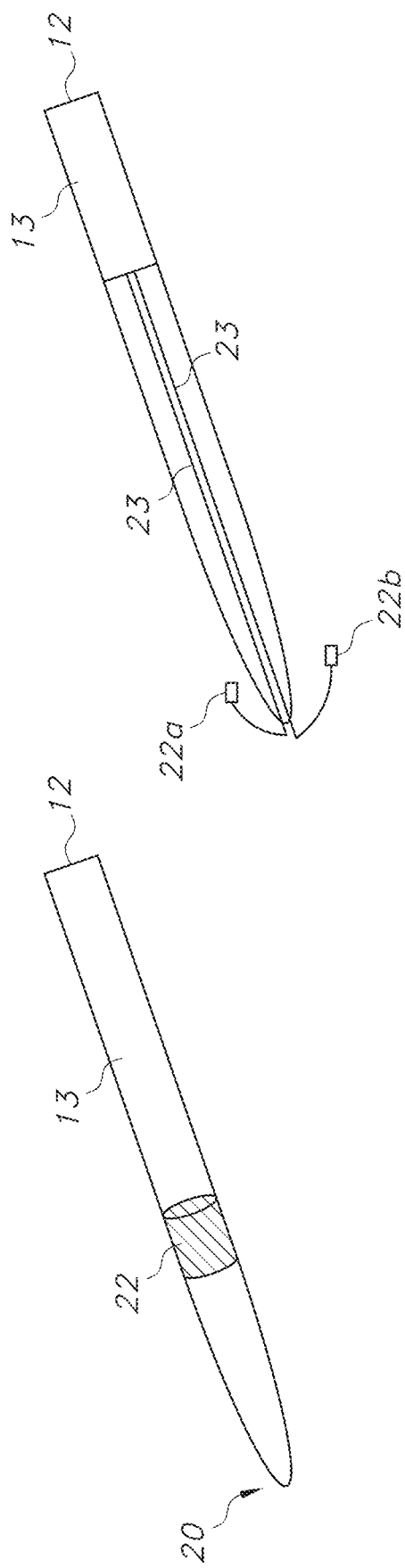
FIG. 8 is a perspective side view of a needle that can be used in conjunction with the EMG subsystem of FIG. 1 and the system of FIG. 4.

For example, as shown in FIG. 1 and FIG. 8, a recording electrode 22 can be present on a shaft 13 of a needle 12, where the needle tip 20 is inserted into a paraspinal muscle 26 such as the medial fascicle 62 of the multifidus muscle 46 so that electrical activity in the muscle 26 (e.g., a motor evoked potential) can be recorded by the EMG subsystem 10 to locate the target nerve near the muscle that is responsible for a patient's pain, position the RF ablation probe near the correct (target) nerve, and determine if a successful lesion has been performed immediately after the RF ablation energy is delivered. In one particular embodiment, for example, the electrode 22 may be offset on the shaft 13 of the needle 12 to allow the needle's tip 20 to contact bone (i.e., the dorsal and medial transverse process 27), while the recording electrode 22 is offset and still positioned with in medial fascicle 62 of the multifidus muscle 46. Further, although the recording electrode 22 in FIG. 8 is shown as having a monopolar configuration, it is to be understood that the recording electrode 22 can have a bipolar or multipolar configuration in other embodiments. For instance, as shown in FIG. 9, the recording electrodes 22a and 22b can be in the form of wires 23 contained within the shaft 13 of the needle 12, where ends of the wires 23 exit the needle 12 in the form of hooks that can be positioned within the medial fascicle 62 of the multifidus muscle 46 to record electrical muscle activity specific to the target nerve (e.g., the medial nerve branch 56 extending from the dorsal ramus 50 when dealing with facet joint pain). However, it is also to be understood that additional recording electrodes can be used, where the hooks or wires can be inserted into the intermediate fascicle 64 and/or lateral fascicle 66 of the multifidus muscle 46, or any other muscle to monitor for electrical muscle activity associated with one or more nerves.

Meanwhile, as shown in FIG. 1 and FIG. 10, recording electrodes 22a and 22b can be present on the shaft 15 of a cannula 14 that is inserted into one or more of the paraspinal muscles 26 to assist in placement of the RF ablation probe 16, where the electrodes 22a and 22b are positioned within the muscle 26 so that electrical activity in the muscle 26 (e.g., a motor evoked potential) can be recorded by the EMG subsystem 10 to determine which nerve near the muscle is responsible for a patient's pain, whether the RF ablation probe has been positioned near the correct (target) nerve, and to determine if a successful lesion has been performed after the RF ablation procedure. For example, during the RF ablation procedure to lesion the medial nerve branch 56 of the dorsal ramus 50, the probe's cannula 14 typically passes through the longissimus muscle 44. Therefore, an electrode 22a or 22b that is placed on the shaft 15 of the cannula 14 can record longissimus muscle 46 activity without necessitating an extra needle stick. Although the recording electrodes 22a and 22b in FIG. 10 have a bipolar configuration, it is to be understood that the recording electrode 22 can have a monopolar or multipolar configuration in other embodiments. Additionally, electrical stimulation can be delivered through the electrodes 22a and 22b to help monitor functionality of the target nerve. That is, the electrical stimulation activates spinal reflexes that transmit through the nerves targeted to treat facet joint pain. Stimulation of the spinal reflexes and recording from the fascicles of the multifidus muscle and paraspinal muscles before and after lesioning enable functional assessment of the nerve targeted for ablation.

In another embodiment, as shown in FIG. 11, the recording electrodes 22c can be in the form of tines that extend from the shaft 214 of the RF ablation probe 16. The tines can be telescopic and/or retractable to allow for the tines to be placed in the desired location in a muscle. The recording electrodes 22c include an uninsulated tip portion 36 at the top of each tine, where each tine extends radially outward from the shaft 214 of the RF ablation probe 16 so that the recording electrodes 22c can reach the medial fascicle 62 of the multifidus muscle 46. Meanwhile the recording electrodes 22c include an uninsulated portion 34 that extends from the shaft to the uninsulated tip portion 36.

Specifically, when certain levels of electrical energy are applied to an area near, around, or on a target nerve via a percutaneous probe via a signal generator, such as one of the probes discussed above, electrical muscle activity EMG measurements of in a muscle near the target nerve can be recorded to measure the amplitude of the corresponding motor evoked potential activity, the latency between the application of the electrical nerve stimulation and the onset of a first MEPs, the latency between the end of one MEP and the start of subsequent MEPs, the frequency of each of the MEPs when bursts of multiple MEPs are present, and as the shape/burst area of the MEPs. Through a quantitative analysis of this information, a target nerve associated with the neural pathway that is the source of pain can be located and identified, after which the target nerve can be blocked and impaired via formation of a lesion on the target nerve to treat the pain.

In addition to the aforementioned EMG monitor 190, the patient monitoring system 160 can also include an electroencephalogram (EEG) monitor 170 and a heart-rate monitor 180 to collect electrocardiogram (ECG) signals. The electroencephalogram monitor 170 can include EEG electrodes 172 coupled with an alternating current (AC) amplifier 200C. The electrodes can be positioned on the scalp of a patient in any suitable manner known to one of ordinary skill in the art such that the electrical activity of any area of the brain can be monitored. The heart-rate monitor 180 can include ECG electrodes 182 coupled with an alternating current (AC) amplifier 200B. Other types of transducers can also be used depending on which physiological parameters are to be monitored. As described, all physiological signals obtained with the patient monitoring system are passed through an AC signal amplifier/conditioner (200A, 200B, 200C). One possible amplifier/conditioner is Model LP511 AC amplifier available from Grass Technologies, a subsidiary of Astro-Med, Inc., West Warwick, R.I., USA.

Isolated Power System

All instruments can be powered by an isolated power supply or system 194 to protect such instruments from ground faults and power spikes carried by the electrical main. One example of an isolated power system is available is the Model IPS115 Isolated Medical-grade Power System from Grass Technologies, a subsidiary of Astro-Med, Inc., West Warwick, R.I., USA.

Controller

A controller 150 is used that can record waveform data and digital information from the patient monitor system 160, such as EMG data, ECG data, EEG data, RF temperature data, etc., and can generate waveform and digital outputs simultaneously for real-time control of the pulse or signal generator 130. Multiple EMG, ECG, and/or EEG recording electrodes can be coupled to the controller via multiple cables, and multiple stimulation/ablation probe electrodes can also be coupled to the controller via multiple cables. The controller 150 can have onboard memory to facilitate high speed data capture, independent waveform sample rates and on-line analysis. An exemplary controller 150 may be a POWER 1401 data-acquisition interface unit available from Cambridge Electronic Design (UK).

Electrical Stimulation Parameters

In the present invention, different electrical stimulation parameters can be used based on the goal of the stimulation. The various stimulation parameters contemplated by the present invention are discussed individually in more detail below.

For example, a first electrical stimulation can be delivered through the active tip of the RF ablation probe, and a trigger signal and stimulation intensity can be passed to data acquisition software for evoked motor potential evaluation. The stimulation may be constant voltage or constant current and can be delivered in a monopolar, bipolar, or multipolar fashion via multiple stimulation channels. Monopolar stimulation may have a grounding pad placed on the patient's skin. Bipolar and multipolar embodiments can have multiple channels positioned at the probe's tip and/or along the probe shaft. The bipolar or multipolar arrangements can help better direct the stimulation and ablation energy towards the intended target nerve (i.e., current steering) and shield non-target nerves from the energy, as described above with respect to FIGS. 11-13C. This can also be done with a monopolar probe tip or electrode that is covered by electrical insulation minus an exposed section that is electrically conductive. The electrodes used for stimulation may be of any shape (i.e., circular, square, triangular, etc.) and size (e.g., 1 mm by 1 mm, 1 mm by 10 mm, etc.) or material, and may optionally serve as a cathode or anode. The probe's tip and stimulation electrodes maybe straight or curved to accommodate various anatomical geometries. Moreover, the electrodes and various channels may be incorporated into a standard or cooled RF ablation probe.

The shape of stimulation waveforms can be variable (i.e., impulses, square-wave pulses, sinusoidal waveforms, etc.) and can be delivered in single bursts or multi-bursts. Multi-burst waveforms (i.e., a train of 5, delivered at about 500 Hz) can have inter-burst frequencies of less than about 1000 Hz. Control software can modulate the stimulation intensities, especially when tracking motor evoked potentials recorded on any channel or can be controlled by the user.

A second electrical stimulation can also be delivered through the electrodes used for EMG recordings, as shown in FIG. 10. The stimulation parameters can be consistent with those described above.

Electrical stimulation through the probe or electrodes located on the cannula can be constant-current or constant-voltage controlled. The stimulation can be delivered in a monopolar, bipolar or multipolar fashion and with monophasic or biphasic waveforms. Single pulse and multi-pulse stimuli may be delivered. Pulse durations are also varied (less than about 5 milliseconds), although shorter pulses widths are preferable (less than about 0.05 milliseconds) since they are less painful and less likely to interfere with the recorded motor evoked potential. Single pulse stimuli can be delivered at frequencies less than about 10 hertz (Hz), and multi-pulse trains can be delivered in less than 10 pulses per train and a train rate of about 1 Hz. Stimulation intensity is less than about 10 milliAmps (mA) or less than about 100 volts (V) with about a 0.01 mA resolution or about a 0.1 V resolution.

Through the system and methods described above, it can be possible to accurately place an RF ablation probe near the painful circuitry (i.e., a target nerve) for subsequent treatment (i.e., ablation), avoid damage to non-target nerves and tissues during treatment (i.e., ablation), identify painful circuitry, and confirm the successful formation of a lesion after treatment in order to alleviate a patient's pain, as discussed in more detail below.

Probe Placement

The present inventors have found that electrical muscle activity (e.g., muscle evoked potentials or MEPs) can be used to demonstrate electrical proximity between an RF ablation probe and the target nerve to be ablated and lesioned. For example, the nerve that is closest to the probe will evoke a burst of EMG activity in the muscles that it innervates with smaller stimulation intensities than nerves that are further away. For example, in the case of RF ablation to treat lumbar facet joint pain, the probe should be manipulated in a direction needed to maximally reduce the stimulation intensity required to elicit a burst of EMG activity in the medial fascicle of the innervated multifidus muscle, which where the medial nerve branch of the dorsal ramus at the same neurological level as the multifidus muscle is the source of the patient's pain.

Preservation of Non-Targeted Nerves and Tissues

In addition, current steering can be used to shape the stimulation and/or ablative field that is delivered by the RF ablation probe. Specifically, the RF ablation probe can be inserted, and the target nerve can be stimulated through the RF ablation probe while recording EMG signals from the surrounding musculature. A medical professional or the patient could then toggle through the various stimulation channels on the RF ablation probe to determine which channels elicit bursts of EMG in the muscles innervated by the target nerve (i.e., the medial fascicle of the multifidus muscle and the medial nerve branch) and non-target nerves (i.e., the longissimus muscle and intermediate nerve branch and/or the iliocostalis muscle and lateral nerve branch). The channel paradigm that evokes EMG bursts in the target nerve and not in the non-target nerves would then indicate that it provides the closest electrical proximity of the RF ablation probe to the target nerve. A stimulation or ablation delivered to the tissue could then be channeled to that specific area to affect the target nerve and preserve the nearby non-target nerves and tissue.

Identification of Painful Circuitry

Disease augments EMG activation patterns, especially pain. The present invention compares EMG activation patterns elicited by nerve stimulation to discern healthy versus painful circuitry, where the painful circuitry can be a target nerve that should be lesioned via RF ablation. For example, bursts of EMG recorded from the medial fascicles of the multifidus muscles in a patient with lumbar facet joint pain may require larger stimulation intensities versus muscles connected to healthy circuitry. Other differences include EMG waveforms, latencies, activation areas, conduction velocities and differences between surrounding muscles (i.e., larger paraspinal muscles).

Confirmation

It has been shown that spinal reflexes can be modulated by electrical stimulation delivered to the paraspinal muscles. That is, if electrical stimulation is delivered to the longissimus muscle, then a reflexive burst of EMG can be found in the nearby paraspinal muscles, including the multifidus and iliocostalis muscles. The operation of this reflex can be used to assess the ablative site following an RF ablation procedure at a target nerve to confirm successful destruction of the target nerve. For example, during the treatment of lumbar facet joint pain, physicians often do not know about the efficacy of the treatment until weeks or months after the procedure. However, the present invention allows the physician to evaluate the integrity of the lesioned site intraoperatively by stimulating a paraspinal muscle (i.e., the longissimus muscle) with intact nervous circuitry and evaluating the burst of EMG in the muscle (i.e., the medial fascicle of the multifidus muscle) innervated by the lesioned nerve (i.e., the medial nerve branch) before and after ablation. The difference in EMG bursts pre-ablation procedure and post-ablation procedure can be used to confirm successful lesion formation. The results of this confirmation step can then be integrated as a feedback loop to the controller such that radiofrequency energy is turned off when the electrical muscle activity (e.g., EMG activity) suggests the target nerve has been lesioned.

Figure 7:
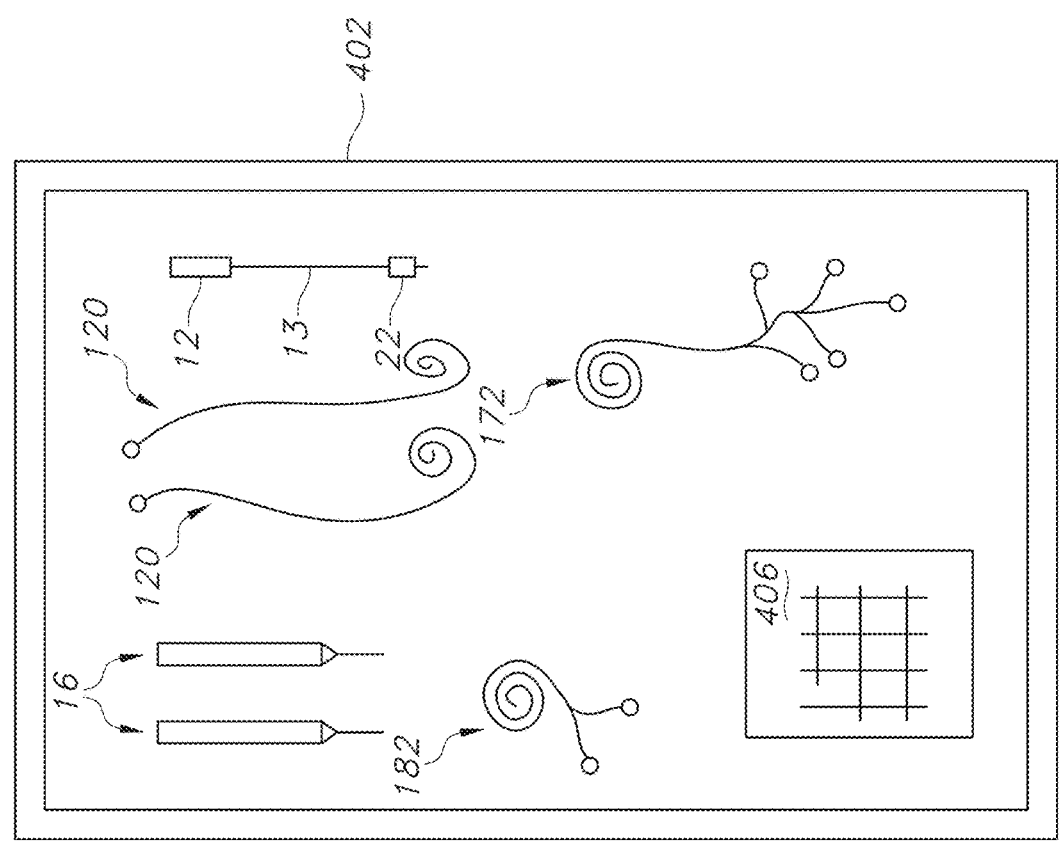
FIG. 7 is a top view of an exemplary kit that may be used in conjunction with the systems and methods contemplated by the present invention.

In addition to the method and system discussed above, the present invention also encompasses a kit for carrying out the various procedures outlined above. FIG. 7 depicts a kit 400 that includes any manner of suitable container 402 in which is provided any combination of the components depicted in FIGS. 1 through 6 and 8 through 14. It should be appreciated that the kit 400 need not contain all of the articles depicted in FIGS. 1 through 6 and 8 through 14. That is, components such as controller, pulse generator, user interface, patient monitoring system, amplifiers or the like need not be included, although suitable probes 16, electrodes such as the EMG recording electrodes 22, EEG electrodes 172, and ECG electrodes 182 may be included in the kit.

The container 402 may be, for example, a suitable tray having a removable sealed covering in which the articles are contained. For example, an embodiment of the kit 400 can include the container 402 with one or more probes 16, one or more needles 12, and one or more electrical leads 120 as discussed above.

The present invention encompasses a kit with any combination of the items utilized to perform the procedure of delivering various frequency levels of electrical nerve stimulation through a percutaneous probe inserted through the skin such that it can be in close proximity to a target nerve thought to be associated with a neural pathway responsible for or the source of pain. For example, the kit 400 may include additional items, such as a drape, site dressings, tape, skin-markers and so forth. The kit 400 may include pre-packaged wipes 406 such as antiseptic wipes or skin-prep wipes.

The present invention also encompasses a method for locating a target nerve thought to be associated with a neural pathway that is the source of pain, verifying that the target nerve has been correctly identified as part of the neural pathway associated with pain, impairing the nerve via ablation/lesioning, and confirming that the target nerve has been successfully impaired. The various steps for carrying out this method are discussed in more detail below.

For example, the method can include locating a first target nerve associated with a facet joint via nerve stimulation and monitoring of electrical muscle activity in a multifidus muscle adjacent the first target nerve is provided, where the multifidus muscle includes a medial fascicle, an intermediate fascicle, and a lateral fascicle. The method also includes inserting a first recording electrode for monitoring electrical muscle activity in the medial fascicle of the multifidus muscle; positioning a first probe comprising an insulated shaft and a first probe electrode located at a distal end of the shaft near the first target nerve, wherein the first probe is housed within a first cannula; generating a first nerve stimulation from a signal generator; delivering the first nerve stimulation to the first target nerve via the first probe electrode; monitoring electrical muscle activity in the medial fascicle of the multifidus muscle via the first recording electrode; and guiding placement of the first probe adjacent the first target nerve based on the electrical muscle activity elicited in the medial fascicle of the multifidus muscle.

The method can further include inserting one or more additional recording electrodes for monitoring electrical muscle activity in the intermediate fascicle, the lateral fascicle, paraspinal muscles surrounding the multifidus muscle, or a combination thereof; and monitoring electrical muscle activity in the intermediate fascicle, the lateral fascicle, paraspinal muscles surrounding the multifidus muscle, or a combination thereof via the one or more additional recording electrodes.

The method can also include guiding placement of the first probe adjacent the first target nerve based on the electrical muscle activity elicited in the intermediate fascicle, the lateral fascicle, paraspinal muscles surrounding the multifidus muscle, or a combination thereof; and preventing placement of the first probe adjacent non-target tissue.

As described above, the first probe electrode can include an array of independent channels for nerve stimulation, nerve ablation, or a combination thereof, each channel having an axial dimension and a radial dimension, wherein each channel is adapted to be separately energized. In such an embodiment, the method can further include selectively activating one or more of the independent channels in the array to direct nerve stimulation energy to the first target nerve. For instance, selectively activating one or more of the independent channels in the array can include delivering a low-level nerve stimulation from each of the one or more independent channels in the array and determining which of the one or more independent channels in the array to activate based on changes in electrical muscle activity latency, burst area, amplitude, or a combination thereof in the medial fascicle as a result of the low-level nerve stimulation.

It is to be understood that monitoring electrical muscle activity in the medial fascicle of the multifidus muscle can include measuring changes in electrical muscle activity latency, burst area, amplitude, or a combination thereof. Further, when the first nerve stimulation is applied at a constant stimulation intensity, a decrease in latency, an increase in burst area, an increase in amplitude, or a combination thereof can indicate that the first probe is in closer proximity to the first target nerve. Meanwhile, when the latency, burst area, amplitude, or a combination thereof are maintained at a constant level, a decrease in the first nerve stimulation intensity can indicate that the first probe is in closer proximity to the first target nerve.

In addition, the method can include locating a second target nerve located at a level cephalad to a level of the first target nerve, wherein the method further includes positioning the first probe near the second target nerve; generating a second nerve stimulation from the signal generator; delivering the second nerve stimulation to the second target nerve via the first probe electrode; monitoring electrical muscle activity in the intermediate fascicle, the lateral fascicle, paraspinal muscles surrounding the multifidus muscle, or a combination thereof via the one or more additional recording electrodes; and guiding placement of the first probe adjacent the second target nerve based on the electrical muscle activity elicited in the intermediate fascicle, the lateral fascicle, paraspinal muscles surrounding the multifidus muscle, or a combination thereof.

Additionally, the method can include locating a second target nerve located at a level cephalad to a level of the first target nerve, wherein the method further includes positioning a second probe comprising an insulated shaft and a second probe electrode located at a distal end of the shaft near the second target nerve, wherein the second probe is housed within a second cannula; generating a second nerve stimulation from the signal generator; delivering the second nerve stimulation to the second target nerve via the second probe electrode; monitoring electrical muscle activity in the intermediate fascicle, the lateral fascicle, paraspinal muscles surrounding the multifidus muscle, or a combination thereof via the one or more additional recording electrodes; and guiding placement of the second probe adjacent the second target nerve based on the electrical muscle activity elicited in the intermediate fascicle, the lateral fascicle, paraspinal muscles surrounding the multifidus muscle, or a combination thereof.

Further, the method can include delivering a third nerve stimulation and monitoring for changes in electrical muscle activity in the medial fascicle elicited as a result of the third nerve stimulation to determine if the first target nerve carries a pain signal. Further, determining that the first target nerve carries the pain signal can include measuring electrical muscle activity latency, burst area, amplitude, or a combination thereof.

Moreover, the method can include forming a lesion on the first target nerve by delivering radiofrequency ablation energy from the first probe. The method can also include confirming successful formation of the lesion on the first target nerve via one or more stimulating electrodes that can be disposed on an outer surface of the first cannula, on a surface of skin, on a percutaneous needle, or a combination thereof. In addition, successful formation of the lesion on the first target nerve can be indicated by a predefined level of change in electrical muscle activity in response to a fourth nerve stimulation. The results of this confirmation step via the fourth nerve stimulation can then be integrated as a feedback loop to the controller such that radiofrequency energy is turned off when the electrical muscle activity (e.g., EMG activity) suggests the target nerve has been lesioned.

As discussed above, the first target nerve can be a medial nerve branch of a dorsal ramus, where electrical muscle activity in the medial fascicle of the multifidus muscle is monitored. However, it is to be understood that electrical muscle activity in intermediate and lateral fascicles of the multifidus muscle as well as electrical muscle activity the longissimus muscle and/or the iliocostalis muscle can also be monitored, respectively, in order to stimulate the first target nerve and/or other target nerves such as the intermediate nerve branch of a dorsal ramus and/or the lateral nerve branch of a dorsal ramus or a target nerve located at a level cephalad to a level of the first target nerve.

The present invention may be better understood with reference to the following examples.

Example 1

It was hypothesized that the visible paraspinal muscle twitch that is currently used intraoperatively to guide placement of an RF ablation probe does not necessarily describe electrical proximity to the target nerve. In Example 1, ultrasonography was used to determine the origin of the visible paraspinal muscle twitch in a human subject undergoing a lumbar, facet joint RF ablation procedure. The probe was placed under fluoroscopic guidance and electrical stimulation was used to 'fine-tune' its placement. Motor stimulation elicited a visible muscle twitch appearing across the subject's lower back. The medical professional accepted the twitch and stimulation threshold to indicate that the probe was in electrical proximity to the target nerve (medial nerve branch). Ultrasonography of the lower back muscles showed that all 3 paraspinal muscles contracted in a time-locked pattern to stimulation. Since the three muscles (multifidus, longissimus, iliocostalis) are innervated by three different nerves (medial nerve branch, intermediate nerve branch, and lateral nerve branch, respectively) that are nearby the ablative site, and because it is understood that stimulation of any one of the nerves with enough intensity could reflexively contract all three muscles, then it could not be determined if the stimulation had activated one or multiple nerves. Ultrasonography was then used to drive the probe towards the target nerve (medial nerve branch). The probe was repositioned and the stimulation intensity was reduced until stimulation elicited a solitary medial fascicle multifidus muscle twitch visible by ultrasound. This approach suggested that the probe was in electrical proximity to target nerve. Importantly, the resultant twitch was visible with ultrasonography, but was not visible by inspection of the subject's lower back. These observations suggest that the visible muscle twitch that is used intraoperatively to place the ablative probe during RF procedures cannot be used to indicate the probe's electrical proximity to the target nerve.

Example 2

Percutaneously placed electrodes were used to selectively record stimulus-elicited bursts of EMG activity from the lumbar medial fascicle of the multifidus muscle and paraspinal muscles (i.e., the longissimus and iliocostalis muscles). The bursts of EMG are hosted by polysegmental spinal reflexes, and can drive all three paraspinal muscles that are ipsilateral and contralateral to the stimulation. The recording and stimulation paradigm described in Example 2 and resulting spinal reflex physiology can be used to facilitate probe placement, and confirmation that the ablative probe has affected the target nerve.

Subjects: 7 subjects (N=7) having a weight ranging from about 55 kilograms to 65 kilograms (kg) were analyzed in this study.

Surgical Preparation: Ketamine (15 milligrams per kilogram) was administered intramuscularly in combination with Xylazine (1 milligram per kilogram) prior to starting the procedure. A face mask of Isoflurane (0.5-5%) in 0.5-2 liters/minute of oxygen as well as an IV of Propofol (2-4 milligrams per kilogram) were also used to aid and/or maintain induction. Finally, Flunixin (1-2 milligrams per kilogram) was given intramuscularly as a pre-operative analgesic. An IV of LRS was administered for the duration of the procedure at the rate of 2.05-5 milliliters per kilogram per hour. Anesthesia was maintained using 0.2-0.6 milligrams per kilograms per hour of Propofol (12-36 milligrams per kilogram per hour) with additional 10 milligrams per kilogram IV boluses of Ketamine administered as needed. At most 1 milliliter of 0.5% Bupivacaine was injected at the stimulation site as a local anesthetic.

Recording Procedures: Bipolar wire hook EMG recording electrodes were placed in the medial fascicles of the multifidus muscles supporting the lumbar spine (levels L2-L5) both ipsilateral and contralateral (levels L3 and L4) to the stimulation site. Recording electrodes were also placed in the longissimus muscles bilaterally (level L3) as well as the iliocostalis muscle (level L3) unilaterally ipsilateral to the stimulation site. All electrodes were placed under ultrasonic guidance.

Ultrasonography and visual inspection of each subject's lower back was used to visualize stimulus elicited muscle contractions.

Stimulation: Two different approaches were used to deliver electrical stimulation to the nerve branches of the dorsal ramus in the lumbar spine. In the first approach (N=3), electrical stimulation was delivered through a standard RF ablation probe (10 millimeter diameter active tip, 20 gauge, 100 millimeter probe shaft) to the lumbar medial nerve branch (L3) of the dorsal ramus. This approach was like those used for treatment of lumbar facet joint pain.

The second approach (N=4) enabled selective stimulation of the three nerve branches and required surgical exposure of the lumbar dorsal ramus. Blunt dissection separated the multifidus and longissimus muscles to expose the medial, intermediate, and lateral nerve branches of the dorsal ramus at L3. A monopolar hook stimulating electrode was used to selectively stimulate each nerve. That is, the electrode was used to gently pull each nerve from the saline filled cavity, such that stimulation was confined to the target nerve. Electrical stimulation used in both approaches consisted of constant-current square-wave pulses (0.2 millisecond pulse width, Digitimer DS5 stimulator) and was delivered in a single pulse and multi-pulse (Train of 5 at a frequency of 500 Hz) paradigm.

In two subjects, electrical stimulation (constant-current square-waves, 1 millisecond pulse width, 10 milliamp intensity) was delivered to the longissimus muscle through subdermal (13 millimeter) needle electrodes. This stimulation was used to test motor reflexes.

Procedure: The stimulation intensity (0.1 milliamps (mA) steps) was varied throughout the procedure to identify motor-thresholds for each of the instrumented muscles. Dye was injected through the ablation probe after the study to confirm placement of the RF ablation probe electrode.

Data Analysis: Electromyography signals were digitized (10,000 Hz, CED Power3 1401) and analyzed with Spike2 software (CED, UK). Each trial consisted of 25 pulses at a constant stimulation intensity. The pulses of each trial were averaged together (centered around the stimulation time) and motor evoked potentials were identified by inspection.

Figure 15:
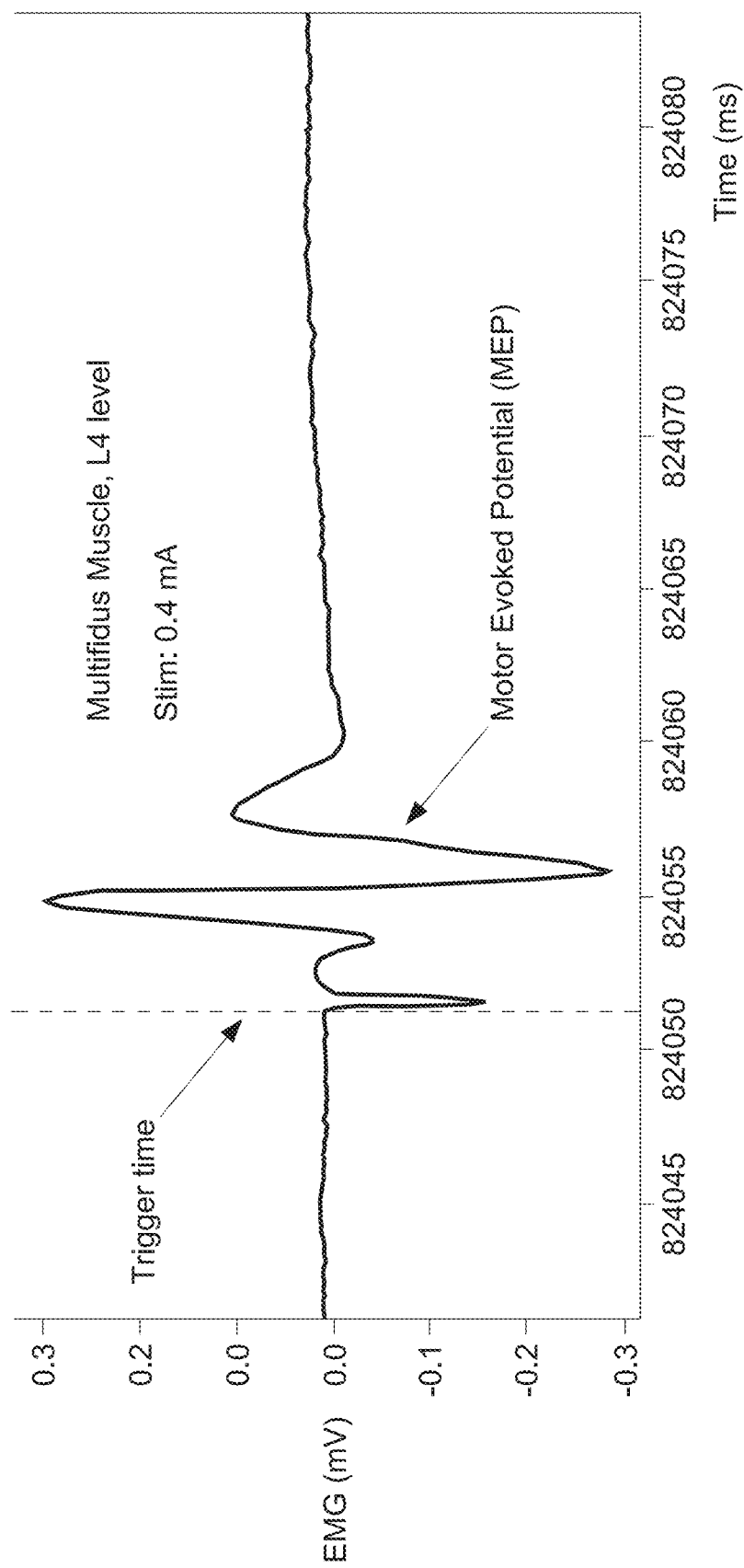
FIG. 15 is a graph illustrating a single motor evoked potential recorded from a medial fascicle of the multifidus muscle and elicited by electrical stimulation of the medial nerve branch as described in Example 2.
Figure 16:
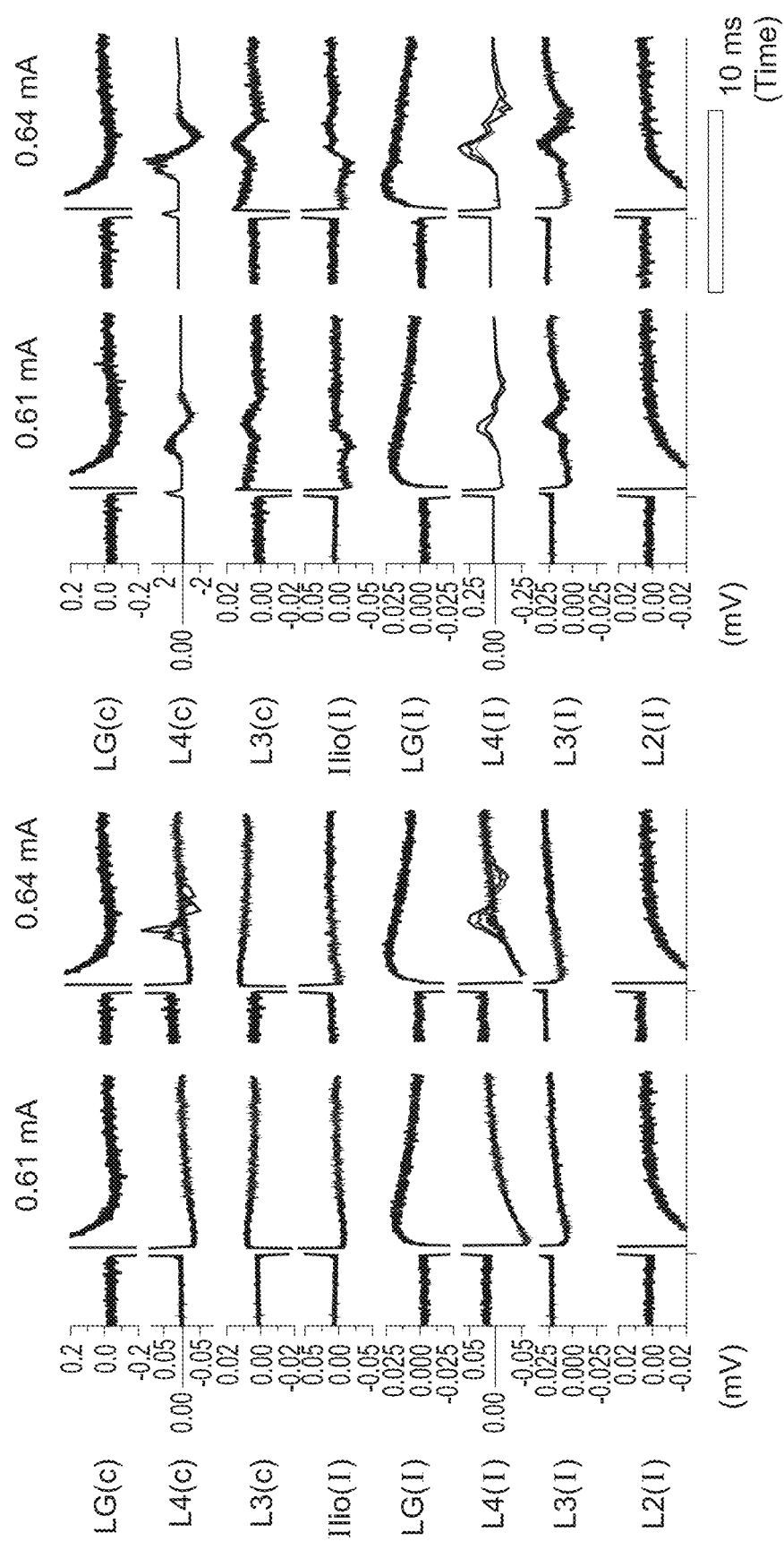
FIG. 16 is a graph illustrating various EMG recordings at four different currents following stimulation of the L3 medial nerve branch as described in Example 2.
Figure 17:
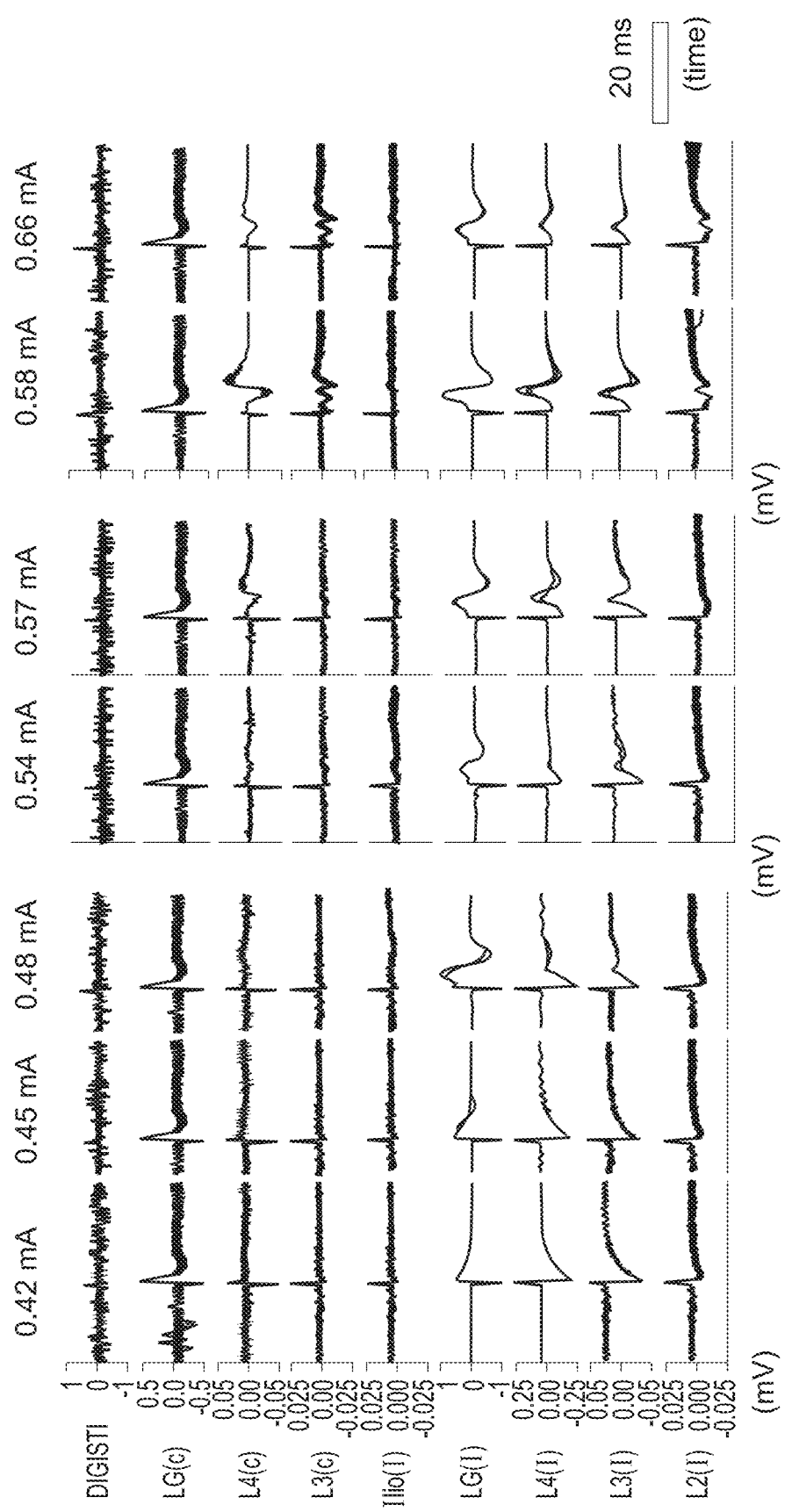
FIG. 17 is a graph illustrating various EMG recordings at seven different currents following stimulation of the L3 intermediate nerve branch as described in Example 2.
Figure 18:
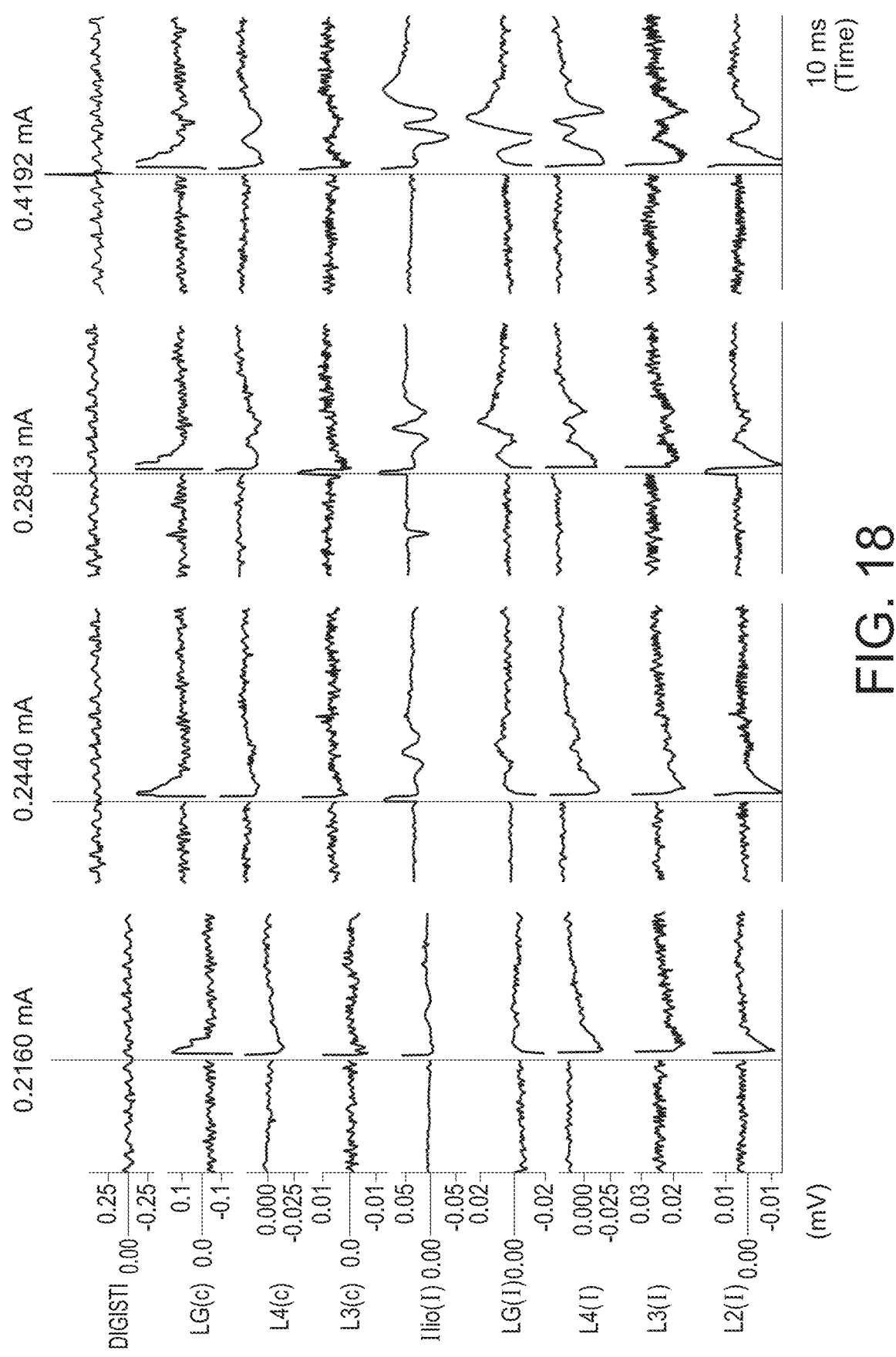
FIG. 18 is a graph illustrating various EMG recordings at four different currents following stimulation of the L3 lateral nerve branch as described in Example 2.

Results: Electrical stimulation through the probe elicited time-locked motor-evoked potentials in the paraspinal muscles, as shown in FIG. 15. The motor evoked potentials appear to be hosted by spinal reflexes since very small increases in stimulation intensities caused muscles at more cephalad and caudal neurological levels to contract, and small increases in stimulation intensity led to bilateral activation patterns, as shown in FIGS. 16-18. Ultrasonography demonstrated that multifidus muscle contraction alone cannot be seen by visual inspection of the subject's back. Visual twitches were seen reliably, however, when the longissimus and iliocostalis muscles were activated.

Selective stimulation of the three nerve branches demonstrated that the muscle innervated by the stimulated nerve will contract at low stimulation intensities See FIG. 16 for stimulation of the L3 medial nerve branch, FIG. 17 for stimulation of the L3 intermediate nerve branch, and FIG. 18 for stimulation of the L3 lateral nerve branch. The dependent variable is EMG, recorded from the multifidus muscles: L2(I), L3(I) and L4(I); longissimus muscles LG(I) and LG(C); and iliocostalis muscles Ilio(I), where the stimulation level is designated as either (I) ipsilateral to stimulation or (C) contralateral to stimulation. As the stimulation intensity is increased, the muscles caudal and cephalad to the stimulated level will contract, followed by those on the contralateral side, and finally the larger paraspinal muscles (longissimus and iliocostalis) will also contract. That is, the multifidus muscles are elicited at the lowest stimulation intensities when the probe is on the medial nerve branch.

This holds true for the longissimus muscle and intermediate nerve branch, and again for the iliocostalis muscle and lateral nerve branch. More intensive stimulation to any nerve branch will elicit spinal reflexes, eventually recruiting all paraspinal muscles. Selective stimulation of the dorsal rami nerves confirms that spinal reflexes host the motor evoked potentials.

Figure 19:
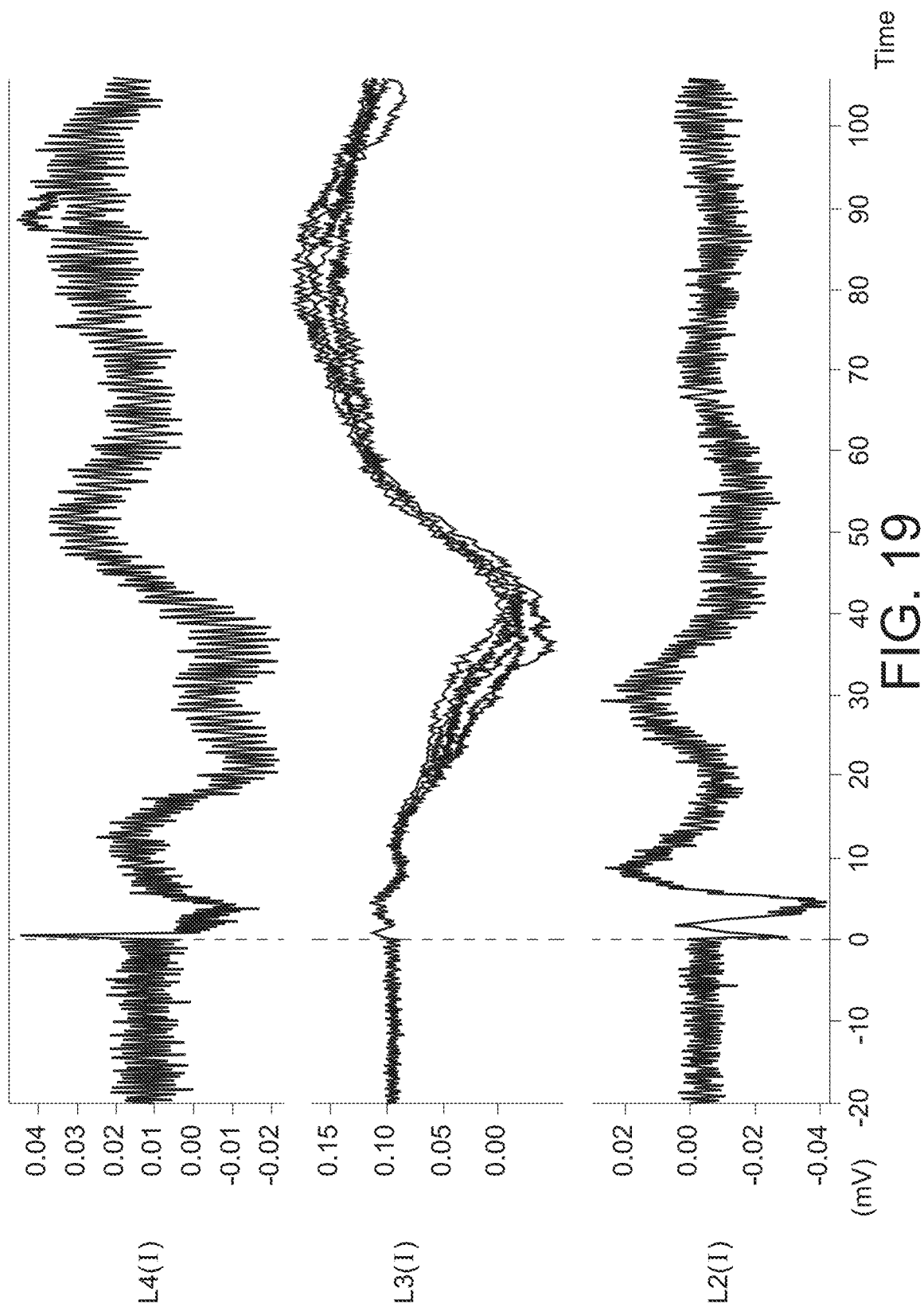
FIG. 19 is a graph illustrating multifidus muscle activation elicited by electrical stimulation to the ipsilateral longissimus muscle as described in Example 2.

Lastly, electrical stimulation of the longissimus muscle in two subjects demonstrated motor evoked potentials in the multifidus muscles, ipsilateral to stimulation, as shown in FIG. 19. This suggests that muscle stimulation may be adequate to elicit spinal reflexes, and a good method of testing nerve block completeness in humans, where a cut-down to hook the target nerve is not possible.

While the present invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A system for locating a first target nerve associated with a facet joint via nerve stimulation and monitoring of electrical muscle activity in a multifidus muscle adjacent the first target nerve, the multifidus muscle comprising a medial fascicle, an intermediate fascicle, and a lateral fascicle, wherein the system comprises:
   a first probe comprising an insulated shaft and a first probe electrode located at a distal end of the insulated shaft, wherein the first probe electrode includes an array of independent channels for nerve stimulation, nerve ablation, or a combination thereof, and wherein the first probe is configured to form a lesion on the first target nerve by delivery of radiofrequency ablation energy;
   a first recording electrode for monitoring electrical muscle activity in the medial fascicle of the multifidus muscle, wherein the first recording electrode is configured for placement in the medial fascicle of the multifidus muscle;
   a signal generator; and
   a controller coupled to the first probe electrode and the first recording electrode, wherein the controller delivers a first nerve stimulation from the signal generator to the first target nerve via the first probe electrode, wherein the controller monitors electrical muscle activity in the medial fascicle via the first recording electrode, wherein proximity of the first probe to the first target nerve is determined by the electrical muscle activity, electromyography (EMG) burst area, and amplitude in the medial fascicle elicited as a result of the first nerve stimulation, wherein the controller provides feedback to a user to guide placement of the first probe adjacent the first target nerve, and wherein the controller is configured to selectively activate one or more of the array of independent channels,
   wherein the controller is configured to: (i) confirm that the first target nerve is a source of pain based, at least in part, on a detected latency between application of the first nerve stimulation and at least one EMG burst in the electrical muscle activity, and (ii) confirm successful formation of the lesion via the first recording electrode based on a difference in electrical muscle activity, EMG burst area, and amplitude elicited by a post-ablation nerve stimulation.

2. The system of claim 1, comprising one or more additional recording electrodes for monitoring electrical muscle activity in the intermediate fascicle, the lateral fascicle, paraspinal muscles surrounding the multifidus muscle, or a combination thereof, wherein the one or more additional recording electrodes are positioned on a first cannula or on a shaft of a needle and configured for placement in the intermediate fascicle, the lateral fascicle, paraspinal muscles surrounding the multifidus muscle, or a combination thereof.

3. The system of claim 2, wherein the controller is configured to monitor for electrical muscle activity in the intermediate fascicle, the lateral fascicle, paraspinal muscles surrounding the multifidus muscle, or a combination thereof, wherein proximity of the first probe to the first target nerve is determined by the electrical muscle activity elicited in the intermediate fascicle, the lateral fascicle, paraspinal muscles surrounding the multifidus muscle, or a combination thereof as a result of the first nerve stimulation, and wherein the controller provides feedback to guide placement of the first probe adjacent the first target nerve and prevent placement of the first probe adjacent non-target tissue.

4. The system of claim 2, wherein the system is configured for locating a second target nerve located at a level cephalad to a level of the first target nerve, wherein the controller is configured to deliver a second nerve stimulation to the second target nerve via the first probe electrode, further wherein the controller is configured to monitor for electrical muscle activity in the intermediate fascicle, the lateral fascicle, paraspinal muscles surrounding the multifidus muscle, or a combination thereof via the one or more additional recording electrodes, wherein proximity of the first probe to the second target nerve is determined by the electrical muscle activity in the intermediate fascicle, the lateral fascicle, paraspinal muscles surrounding the multifidus muscle, or a combination thereof elicited as a result of the second nerve stimulation, and wherein the controller provides feedback to guide placement of the first probe adjacent the second target nerve and to prevent placement of the first probe adjacent non-target tissue.

5. The system of claim 2, further comprising a second probe comprising an insulated shaft and a second probe electrode located at a distal end of the shaft, wherein the second probe is housed within a second cannula, wherein the system is configured for locating a second target nerve located at a level cephalad to a level of the first target nerve, wherein the controller is configured to deliver a second nerve stimulation to the second target nerve via the second probe electrode, further wherein the controller is configured to monitor for electrical muscle activity in the intermediate fascicle, the lateral fascicle, paraspinal muscles surrounding the multifidus muscle, or a combination thereof via the one or more additional recording electrodes, wherein proximity of the second probe to the second target nerve is determined by the electrical muscle activity in the intermediate fascicle, the lateral fascicle, paraspinal muscles surrounding the multifidus muscle, or a combination thereof elicited as a result of the second nerve stimulation, and wherein the controller provides feedback to a user to guide placement of the second probe adjacent the second target nerve and to prevent placement of the second probe adjacent non-target tissue.

6. The system of claim 2, wherein the one or more additional recording electrodes has a monopolar configuration, a bipolar configuration, or a multipolar configuration.

7. The system of claim 2, wherein the one or more additional recording electrodes are disposed on the shaft of the needle and offset from a tip of the needle.

8. The system of claim 2, wherein the one or more additional recording electrodes is disposed on an outer surface of the first cannula.

9. The system of claim 2, wherein the first probe is configured to form a lesion on the first target nerve by delivery of radiofrequency ablation energy,
wherein the system confirms successful formation of the lesion via the first recording electrode, the one or more additional recording electrodes, or a combination thereof,
wherein the one or more additional recording electrodes monitor electrical muscle activity in the medial fascicle, the intermediate fascicle, the lateral fascicle, paraspinal muscles surrounding the multifidus muscle, or a combination thereof, and
wherein the one or more additional recording electrodes are configured for placement in the medial fascicle, the intermediate fascicle, the lateral fascicle, paraspinal muscles surrounding the multifidus muscle, or a combination thereof.

10. The system of claim 1, wherein the first recording electrode has a monopolar configuration, a bipolar configuration, or a multipolar configuration.

11. The system of claim 1, wherein one or more recording electrodes are disposed on the first probe at the distal end of the insulated shaft, wherein the first recording electrode includes a tine extending from the insulated shaft, and wherein the tine is telescopic or retractable from the insulated shaft to allow the tine to be placed in a desired location.

12. The system of claim 1, wherein the first probe electrode has a monopolar configuration, a bipolar configuration, or a multipolar configuration.

13. The system of claim 1, wherein monitoring electrical muscle activity in the medial fascicle comprises measuring changes in electrical muscle activity latency, burst area EMG, and amplitude, wherein the first nerve stimulation is applied at a constant stimulation intensity, wherein: (i) a decrease in the latency, an increase in the EMG burst area, an increase in the amplitude, or a combination thereof between two points in time indicates that the first probe is in closer proximity to the first target nerve, or (ii) when the latency, EMG burst area, and amplitude, are constant between two points in time, a decrease in intensity of the first nerve stimulation indicates that the first probe is in closer proximity to the first target nerve.

14. The system of claim 1, wherein the system determines if the first target nerve carries a pain signal by monitoring for changes in electrical muscle activity in the medial fascicle elicited as a result of the first nerve stimulation, wherein determining that the first target nerve carries the pain signal comprises measuring electrical muscle activity latency, EMG burst area, and amplitude.

15. The system of claim 1, wherein the first probe includes a sharp tip at the distal end for navigating through tissue.

16. The system of claim 1, wherein the first probe is configured to form a lesion on the first target nerve by delivery of radiofrequency ablation energy.

17. The system of claim 16, further comprising one or more stimulating electrodes which are disposed on the first probe, an outer surface of a first cannula, on a surface of skin, on a percutaneous needle, or a combination thereof,
wherein the system confirms successful formation of the lesion via the first nerve stimulation and the one or more stimulating electrodes, wherein the one or more stimulating electrodes are disposed on the first probe, an outer surface of the first cannula, on a surface of skin, on a percutaneous needle, or a combination thereof,
wherein the controller provides feedback to the user indicating successful formation of the lesion on the first target nerve based on a predefined level of change in electrical muscle activity and wherein delivery of radiofrequency energy from the first probe is discontinued upon confirming successful formation of the lesion on the first target nerve.

18. The system of claim 1, wherein the first target nerve is a medial nerve branch of a dorsal ramus.

19. The system of claim 1, wherein the system is configured to generate a sound or visual indicator to indicate electrical proximity to the first target nerve.

20. A method for locating a first target nerve associated with a facet joint via nerve stimulation and monitoring of electrical muscle activity in a multifidus muscle adjacent the first target nerve, the multifidus muscle comprising a medial fascicle, an intermediate fascicle, and a lateral fascicle, the method comprising:
inserting a plurality of recording electrodes for monitoring electrical muscle activity in the medial fascicle of the multifidus muscle, wherein the plurality of recording electrodes are positioned on a first cannula;
positioning a first probe within the first cannula and thereby in proximity to the first target nerve, the first probe comprising an insulated shaft and a first probe electrode located at a distal end of the insulated shaft, wherein the first probe electrode includes an array of independent channels for nerve stimulation, nerve ablation, or a combination thereof, wherein each channel is configured to be selectively activated based on changes in electrical muscle activity latency, EMG burst area, and amplitude in the medial fascicle;
generating a first nerve stimulation from a signal generator;
delivering the first nerve stimulation to the first target nerve via the first probe electrode;
monitoring electrical muscle activity in the medial fascicle of the multifidus muscle via the plurality of recording electrodes on the first cannula;
guiding placement of the first probe adjacent the first target nerve based on the electrical muscle activity elicited in the medial fascicle of the multifidus muscle;
confirming that the first target nerve is a source of pain based, at least in part, on a detected latency between application of the first nerve stimulation and at least one EMG burst in the electrical muscle activity;
forming a lesion on the first target nerve by delivery of radiofrequency ablation energy; and
confirming successful formation of the lesion via at least one recording electrode based on a difference in electrical muscle activity, EMG burst area, and amplitude elicited by a post-ablation nerve stimulation.

21. The method of claim 20, further comprising:
inserting one or more additional recording electrodes for monitoring electrical muscle activity in the intermediate fascicle, the lateral fascicle, paraspinal muscles surrounding the multifidus muscle, or a combination thereof; and
monitoring electrical muscle activity in the intermediate fascicle, the lateral fascicle, paraspinal muscles surrounding the multifidus muscle, or a combination thereof via the one or more additional recording electrodes.

22. The method of claim 21, further comprising:
  guiding placement of the first probe adjacent the first target nerve based on the electrical muscle activity elicited in the intermediate fascicle, the lateral fascicle, paraspinal muscles surrounding the multifidus muscle, or a combination thereof; and
  preventing placement of the first probe adjacent non-target tissue.

23. The method of claim 21, wherein the method comprises locating a second target nerve located at a level cephalad to a level of the first target nerve, wherein the method further comprises:
  positioning the first probe near the second target nerve;
  generating a second nerve stimulation from the signal generator;
  delivering the second nerve stimulation to the second target nerve via the first probe electrode;
  monitoring electrical muscle activity in the intermediate fascicle, the lateral fascicle, paraspinal muscles surrounding the multifidus muscle, or a combination thereof via the one or more additional recording electrodes; and
  guiding placement of the first probe adjacent the second target nerve and preventing placement of the first probe adjacent non-target tissue based on the electrical muscle activity elicited in the intermediate fascicle, the lateral fascicle, paraspinal muscles surrounding the multifidus muscle, or a combination thereof.

24. The method of claim 21, wherein the method comprises locating a second target nerve located at a level cephalad to a level of the first target nerve, wherein the method further comprises:
  positioning a second probe comprising an insulated shaft and a second probe electrode located at a distal end of the insulated shaft near the second target nerve, wherein the second probe is housed within a second cannula;
  generating a second nerve stimulation from the signal generator;
  delivering the second nerve stimulation to the second target nerve via the second probe electrode;
  monitoring electrical muscle activity in the intermediate fascicle, the lateral fascicle, paraspinal muscles surrounding the multifidus muscle, or a combination thereof via the one or more additional recording electrodes; and
  guiding placement of the second probe adjacent the second target nerve and preventing placement of the second probe adjacent non-target tissue based on the electrical muscle activity elicited in the intermediate fascicle, the lateral fascicle, paraspinal muscles surrounding the multifidus muscle, or a combination thereof.

25. The method of claim 20, wherein the first probe electrode includes an array of independent channels for nerve stimulation, nerve ablation, or a combination thereof, each channel having an axial dimension and a radial dimension, wherein each channel is adapted to be separately energized.

26. The method of claim 25, wherein the method comprises selectively activating one or more of the independent channels in the array to direct nerve stimulation energy to the first target nerve.

27. The method of claim 20, comprising applying the first nerve stimulation at a constant stimulation intensity, wherein a decrease in latency, an increase in EMG burst area, an increase in amplitude, or a combination thereof indicates that the first probe is in closer proximity to the first target nerve, or comprising maintaining the latency, EMG burst area, amplitude, or a combination thereof at a constant level, wherein a decrease in the first nerve stimulation intensity indicates that the first probe is in closer proximity to the first target nerve.

28. The method of claim 20, comprising:
  delivering a third nerve stimulation; and
  monitoring for changes in electrical muscle activity in the medial fascicle elicited as a result of the third nerve stimulation to determine if the first target nerve carries a pain signal, wherein determining that the first target nerve carries the pain signal comprises measuring electrical muscle activity latency, EMG burst area, and amplitude.

29. The method of claim 20, further comprising:
  forming a lesion on the first target nerve by delivering radiofrequency ablation energy from the first probe, wherein successful formation of the lesion is confirmed via the first recording electrode, one or more additional recording electrodes, or a combination thereof, wherein the one or more additional recording electrodes monitor electrical muscle activity in the medial fascicle, the intermediate fascicle, the lateral fascicle, paraspinal muscles surrounding the multifidus muscle, or a combination thereof, wherein the one or more additional recording electrodes are configured for placement in the medial fascicle, the intermediate fascicle, the lateral fascicle, paraspinal muscles surrounding the multifidus muscle, or a combination thereof.

30. The method of claim 29, further comprising:
  confirming successful formation of the lesion on the first target nerve via a fourth nerve stimulation and one or more stimulating electrodes, wherein the one or more stimulating electrodes are disposed on a probe, an outer surface of the first cannula, on a surface of skin, on a percutaneous needle, or a combination thereof.

31. The method of claim 30, wherein successful formation of the lesion on the first target nerve is indicated by a predefined level of change in electrical muscle activity, wherein delivering radiofrequency ablation energy from the first probe is discontinued upon confirming successful formation of the lesion on the first target nerve.

32. The method of claim 20, wherein a sound or visual indicator is generated to indicate electrical proximity to the first target nerve.

33. A system for locating a first target nerve associated with a facet joint via nerve stimulation and monitoring of electrical muscle activity in a multifidus muscle adjacent the first target nerve, the multifidus muscle comprising a medial fascicle, an intermediate fascicle, and a lateral fascicle, wherein the system comprises:
  a first probe comprising an insulated shaft and a first probe electrode located at a distal end of the insulated shaft, wherein the first probe electrode includes an array of independent channels for nerve stimulation, nerve ablation, or a combination thereof, wherein the first probe is configured to form a lesion on the first target nerve by delivery of radiofrequency ablation energy;
  a plurality of recording electrodes for monitoring electrical muscle activity in the medial fascicle of the multifidus muscle, wherein plurality of recording electrodes is configured for placement in the medial fascicle of the multifidus muscle;
  a signal generator; and
  a controller coupled to the first probe electrode and the plurality of recording electrodes, wherein the controller delivers a first nerve stimulation from the signal generator to the first target nerve via the first probe electrode, wherein the controller monitors electrical muscle activity in the medial fascicle via the plurality of recording electrodes, wherein proximity of the first probe to the first target nerve is determined by the electrical muscle activity in the medial fascicle elicited as a result of the first nerve stimulation, and wherein the controller provides feedback to a user to guide placement of the first probe adjacent the first target nerve, and wherein the controller is configured to selectively activate one or more of the array of independent channels, wherein the controller is configured to: (i) confirm that the first target nerve is a source of pain based, at least in part, on a detected latency between application of the first nerve stimulation and at least one electromyography (EMG) burst in the electrical muscle activity, and (ii) confirm successful formation of the lesion via at least one recording electrode based on a difference in electrical muscle activity, EMG burst area, and amplitude elicited by a post-ablation nerve stimulation.

\* \* \* \* \*